(12) United States Patent
Reik

(10) Patent No.: US 10,808,020 B2
(45) Date of Patent: Oct. 20, 2020

(54) NUCLEASE-MEDIATED REGULATION OF GENE EXPRESSION

(71) Applicant: Sangamo Therapeutics, Inc., Richmond, CA (US)

(72) Inventor: Andreas Reik, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 109 days.

(21) Appl. No.: 15/565,811

(22) PCT Filed: May 12, 2016

(86) PCT No.: PCT/US2016/032049
§ 371 (c)(1),
(2) Date: Oct. 11, 2017

(87) PCT Pub. No.: WO2016/183298
PCT Pub. Date: Nov. 17, 2016

(65) Prior Publication Data
US 2018/0111975 A1    Apr. 26, 2018

Related U.S. Application Data

(60) Provisional application No. 62/303,595, filed on Mar. 4, 2016, provisional application No. 62/160,396, filed on May 12, 2015.

(51) Int. Cl.
| | |
|---|---|
| *C12N 9/22* | (2006.01) |
| *A61K 48/00* | (2006.01) |
| *C07K 14/705* | (2006.01) |
| *C07K 14/46* | (2006.01) |
| *C12N 5/0789* | (2010.01) |
| *A61K 38/00* | (2006.01) |

(52) U.S. Cl.
CPC ............ *C07K 14/705* (2013.01); *C07K 14/46* (2013.01); *C12N 5/0647* (2013.01); *C12N 9/22* (2013.01); *A61K 38/00* (2013.01); *C12N 2501/20* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,794,136 B1 | 9/2004 | Eisenberg et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,074,596 B2 | 7/2006 | Darzynkiewicz et al. | |
| 7,153,949 B2 | 12/2006 | Kim et al. | |
| 7,163,824 B2 | 1/2007 | Cox, III et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,888,121 B2 | 2/2011 | Urnov et al. | |
| 7,914,796 B2 | 3/2011 | Miller et al. | |
| 7,951,925 B2 | 5/2011 | Ando et al. | |
| 7,972,854 B2 | 7/2011 | Miller et al. | |
| 8,034,598 B2 | 10/2011 | Miller | |
| 8,110,379 B2 | 2/2012 | DeKelver et al. | |
| 8,153,773 B2 | 4/2012 | Jemielity et al. | |
| 8,409,861 B2 | 4/2013 | Guschin et al. | |
| 8,586,526 B2 | 11/2013 | Gregory et al. | |
| 8,623,618 B2 | 1/2014 | Doyon et al. | |
| 8,703,489 B2 | 4/2014 | Wang | |
| 8,772,453 B2 | 7/2014 | Paschon et al. | |
| 8,945,868 B2 | 2/2015 | Collingwood et al. | |
| 8,956,828 B2 | 2/2015 | Bonini et al. | |
| 9,005,973 B2 | 4/2015 | Cost et al. | |
| 9,045,763 B2 | 6/2015 | DeKelver et al. | |
| 9,150,847 B2 | 10/2015 | Rebar | |
| 9,200,266 B2 | 12/2015 | Wang | |
| 9,255,250 B2 | 2/2016 | Gregory et al. | |
| 2003/0068675 A1 | 4/2003 | Liu et al. | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2005/0267061 A1 | 12/2005 | Martin | |

(Continued)

FOREIGN PATENT DOCUMENTS

| | | |
|---|---|---|
| GB | 2338237 A | 12/1999 |
| WO | WO 95/19431 | 7/1995 |

(Continued)

OTHER PUBLICATIONS

Bauer, et al., "An Erythroid Enhancer of BCL11A Subject to Genetic Variation Determines Fetal Hemoglobin Level," *Science* 342:253-257 (2013).

(Continued)

*Primary Examiner* — Ileana Popa
(74) *Attorney, Agent, or Firm* — Pasternak Patent Law

(57) ABSTRACT

The present disclosure is in the field of genome engineering, particularly targeted modification of the genome of a hematopoietic cell.

25 Claims, 17 Drawing Sheets
Specification includes a Sequence Listing.

(56) References Cited

U.S. PATENT DOCUMENTS

| | | |
|---|---|---|
| 2006/0063231 A1 | 3/2006 | Li et al. |
| 2006/0188987 A1 | 8/2006 | Guschin et al. |
| 2007/0111312 A1 | 5/2007 | Schiedner et al. |
| 2007/0218528 A1 | 9/2007 | Miller |
| 2008/0131962 A1 | 6/2008 | Miller |
| 2008/0159996 A1 | 7/2008 | Ando et al. |
| 2008/0299580 A1 | 12/2008 | DeKelver et al. |
| 2009/0068164 A1 | 3/2009 | Segal et al. |
| 2009/0305419 A1 | 12/2009 | Miller |
| 2010/0047805 A1 | 2/2010 | Wang |
| 2010/0218264 A1 | 8/2010 | Cui et al. |
| 2011/0082093 A1 | 4/2011 | Gregory et al. |
| 2011/0182867 A1 | 7/2011 | Orkin et al. |
| 2011/0201055 A1 | 8/2011 | Doyon |
| 2011/0207221 A1 | 8/2011 | Cost et al. |
| 2011/0265198 A1 | 10/2011 | Gregory et al. |
| 2011/0301073 A1 | 12/2011 | Gregory et al. |
| 2012/0017290 A1 | 1/2012 | Cui et al. |
| 2012/0192301 A1 | 7/2012 | Jaenisch et al. |
| 2012/0195936 A1 | 8/2012 | Rudolph et al. |
| 2013/0122591 A1 | 5/2013 | Cost et al. |
| 2013/0137104 A1 | 5/2013 | Cost et al. |
| 2013/0177983 A1 | 7/2013 | Rebar |
| 2013/0196373 A1 | 8/2013 | Gregory et al. |
| 2013/0326645 A1 | 12/2013 | Cost et al. |
| 2014/0080216 A1 | 3/2014 | Cost et al. |
| 2014/0161873 A1 | 6/2014 | Bancel et al. |
| 2015/0056705 A1 | 2/2015 | Conway et al. |
| 2015/0064789 A1 | 3/2015 | Paschon et al. |
| 2015/0132269 A1 | 5/2015 | Orkin et al. |
| 2015/0335708 A1 | 11/2015 | Froelich et al. |

FOREIGN PATENT DOCUMENTS

| | | |
|---|---|---|
| WO | WO 96/06166 | 2/1996 |
| WO | WO 98/37186 | 8/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 00/27878 | 5/2000 |
| WO | WO 01/60970 | 8/2001 |
| WO | WO 01/88197 | 11/2001 |
| WO | WO 02/016536 | 2/2002 |
| WO | 2002042459 A2 | 5/2002 |
| WO | WO 02/077227 | 10/2002 |
| WO | WO 02/099084 | 12/2002 |
| WO | WO 03/016496 | 2/2003 |
| WO | WO 2009/042163 | 4/2009 |
| WO | WO 2010/030963 | 3/2010 |
| WO | WO 2013/179211 | 12/2013 |
| WO | 2014036219 A2 | 3/2014 |
| WO | WO 2014/085593 | 6/2014 |
| WO | 2015073683 A2 | 5/2015 |
| WO | 2016182917 A1 | 11/2016 |
| WO | 2017115268 A1 | 7/2017 |
| WO | 2017182881 A2 | 10/2017 |

OTHER PUBLICATIONS

Beerli, et al., "Engineering Polydactyl Zinc-Finger Transcription Factors," *Nature Biotechnology* 20:135-141 (2002).

Canver, et al., "BCL11A Enhancer Dissection by CAS9-Mediated In Situ Saturating Mutagenesis," *Nature* 527(7577):192-197 (2015).

Choo, et al., "Advances in Zinc Finger Engineering," *Current Opinion in Structural Biology* 10:411-416 (2000).

Constantoulakis, et al., "Alpha-Amino-N-Butyric Acid Stimulates Fetal Hemoglobin in the Adult," *Blood* 72(6):1961-1967 (1988).

DeSimone, "5-Azacytidine Stimulates Fetal Hemoglobin Synthesis in Anemic Baboons," *Proc Nat'l Acad Sci USA* 79(14):4428-4431 (1982).

Gabriel, et al., "An Unbiased Genome-Wide Analysis of Zinc-Finger Nuclease Specificity," *Nat Biotech* 29(9):816-823 (2011).

Giarratana, et al., "Proof of Principle for Transfusion of In Vitro—Generated Red Blood Cells," *Blood* 118(19):5071-5079 (2011).

Guillinger, et al., "Fusion of Catalytically Inactive CAS9 to FOKI Nuclease Improves the Specificity of Genome Modification," *Nature Biotech.* 32(6):577-582 (2014).

Guo, et al., "Directed Evolution of an Enhanced and Highly Efficient FOKl Cleavage Domain for Zinc Finger Nucleases," *J. Mol. Biol.* 400(1):96-107 (2010).

Guschin, et al., "A Rapid and General Assay for Monitoring Endogenous Gene Modification," *Methods Mol Biol.* 649:247-256 (2010).

Isalan, et al., "A Rapid, Generally Applicable Method to Engineer Zinc Fingers Illustrated by Targeting the HIV-1 Promoter," *Nat Biotechnol.* 19(7):656-660 (2001).

Karikó, et al., "Incorporation of Pseudouridine into MRNA Yields Superior Nonimmunogenic Vector With Increased Translational Capacity and Biological Stability," *Molecular Therapy* 16(11):1833-1844 (2012).

Kormann, et al., "Expression of Therapeutic Proteins After Delivery of Chemically Modified MRNA in Mice," *Nature Biotechnology* 29(2):154-157 (2011).

Ley, et al., "5-Azacytidine Selectively Increases γ-Globin Synthesis in a Patient With β$^+$Thalassemia," *N. Engl. J. Medicine* 307(24):1469-1475 (1982).

Ley, et al., "5-Azacytidine Increases γ-Globin Synthesis and Reduces the Proportion of Dense Cells in Patients With Sickle Cell Anemia," *Blood* 62(2):370-380 (1983).

Matson, et al., "Transcriptional Regulatory Elements in the Human Genome," *Ann Rev Genome Hum Genet* 7:29-59 (2006).

McCaffery, et al., "CRISPR-CAS9 D10A Nickase Target-Specific Fluorescent Labeling of Double Strand DNA for Whole Genome Mapping and Structural Variation Analysis," *Nucleic Acids Res.* 44(2):e11.doi:10.1093/nar/gkv878. (2016).

Miller, et al., "An Improved Zinc-Finger Nuclease Architecture for Highly Specific Genome Editing," *Nat. Biotechnol.* 25(7):778-785 (2007).

Orlando, et al., "Zinc-Finger Nuclease-Driven Targeted Integration into Mammalian Genomes Using Donors With Limited Chromosomal Homology," *Nucleic Acids Res.* 38(15):e152 (2010).

Pabo, et al., "Design and Selection of Novel CYS2-HIS2 Zinc Finger Proteins," *Ann. Rev. Biochem.* 70:313-340 (2001).

Perez, et al., "Establishment of HIV-1 Resistance in CD4$^+$T Cells by Genome Editing Using Zinc-Finger Nucleases," *Nat. Biotechnol* 26(7):808-816 (2008).

Sankaran, et al., "Human Fetal Hemoglobin Expression is Regulated by the Developmental Stage-Specific Repressor BCL11A," *Science* 322:1839-1842 (2008).

Segal, et al., "Custom DNA-Binding Proteins Come of Age: Polydactyl Zinc-Finger Proteins," *Current Opinion Biotechnology* 12:632-637 (2001).

Sharma, et al., "In Vivo Genome Editing of the Albumin Locus as a Platform for Protein Replacement Therapy," *Blood* 126(15):1777-1784 with online supplementary materials (2015).

Sheng, et al., "Structure-Based Cleavage Mechanism of Thermus Thermophilus Argonaute DNA Guide Strand-Mediated DNA Target Cleavage," *Proc. Natl. Aca. Sci. U.S.A.* 111(2):652-657 (2014).

Swarts, et al., "DNA-Guided DNA Interference by a Prokaryotic Argonaute," *Nature* 507(7491):258-261 doi:10.1038/nature12971 (2014).

Tebas, et al., "Gene Editing of CCR5 in Autologous CD4 T Cells of Persons Infected With HIV," *The New England Journal of Medicine* 370(10):901 (2014).

Thein, et al., "Control of Fetal Hemoglobin: New Insights Emerging From Genomics and Clinical Implications," *Hum. Mol. Genet.* 18(R2):R216-R223 (2009).

Tsai, et al., "Defining and Improving the Genome-Wide Specificities of CRISPR-CAS9 Nucleases," *Nature Reviews Genetics* 17:300-312 (2016).

Vierstra, et al., "Functional Footprinting of Regulatory DNA," *Nat Methods* 12(10):927-930 (2015).

(56) References Cited

OTHER PUBLICATIONS

Yannaki, et al., "Hematopoietic Stem Cell Mobilization for Gene Therapy of Adult Patients with Severe B-Thalassemia: Results of Clinical Trials Using G-CSF or Plerixafor in Splenectomized and Nonsplenectomized Subjects," *Mol Ther* 20(1):230-238 (2012).

Reik, et al., "From GWAS to the Clinic: Genome-Editing the Human BCL11A Erythroid Enhancer for Fetal Globin Elevation in the Hemoglobinopathies," Molecular Therapy, vol. 23, No. Supp 1, pp. 523-524 (2015).

Petersen, et al., "Advances in Genetic Modification of Farm Animals Using Zinc-Finger Nucleases (ZFN)," Chromosome Res. 23:7-15 (2015).

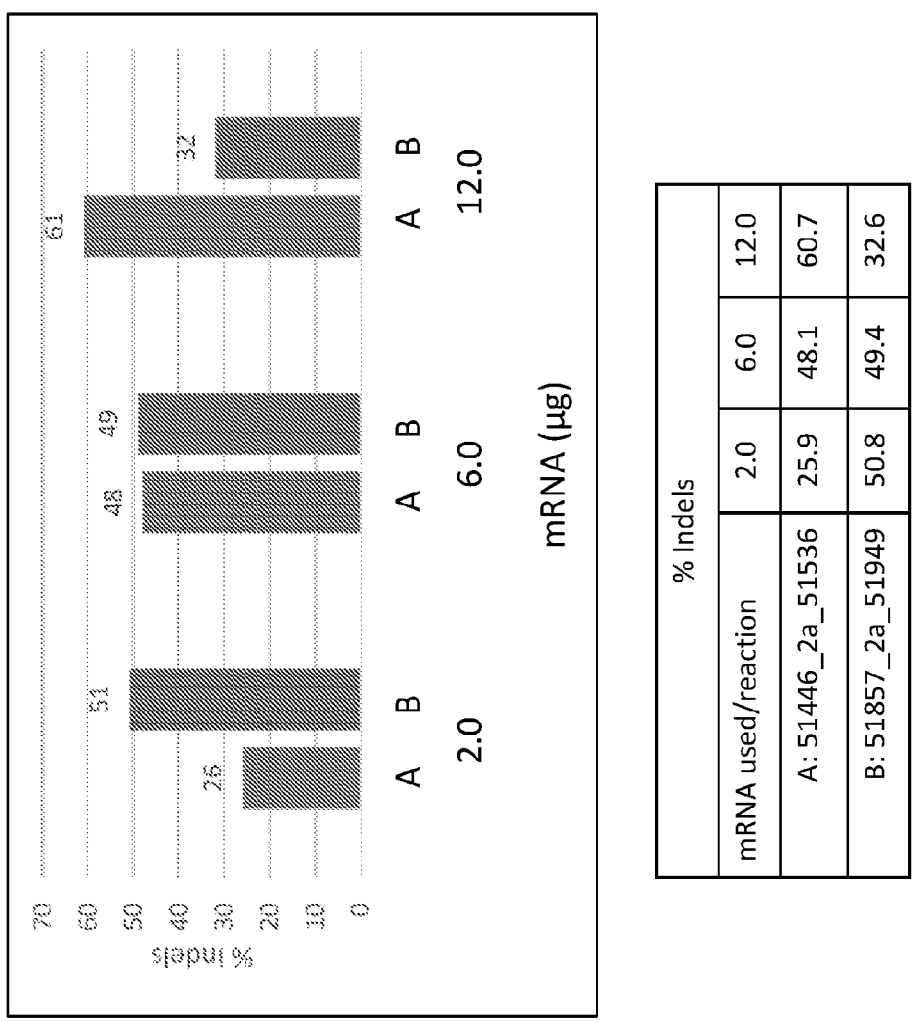

Figure 10A

| amplicon_location | treated_indel_bonferroni_pva freq | lue | genic | coding | gene | location |
|---|---|---|---|---|---|---|
| chr2:60722338-60722476 | 63.261% | 0.00000 | | | LRRC1 | intron |
| chr6:53670690-53670868 | 2.312% | 0.00000 | y | n | LHX1 | intron |
| chr17:35295932-35296095 | 1.184% | 0.00000 | y | n | n/a | intergenic |
| chr8:140226152-140226311 | 0.711% | 0.00000 | n | n | MMP27 | upstream |
| chr11:102556535-102556674 | 0.344% | 0.00000 | n | n | COMMD6 | exon 1 |
| chr13:76123418-76123581 | 0.674% | 0.00000 | y | n | DSCC1 | upstream |
| chr8:120868614-120868752 | 0.303% | 0.00000 | n | n | ACOT11 | upstream |
| chr1:54972397-54972573 | 0.569% | 0.00000 | n | n | INPP5A | intron |
| chr10:134468242-134468405 | 0.425% | 0.00000 | y | n | ZMAT3 | downstream |
| chr3:178716601-178716740 | 0.117% | 0.00029 | n | n | MIR5093 | intergenic |
| chr16:85350785-85350924 | 0.156% | 0.00045 | y | n | DUSP14 | intron |
| chr17:35861457-35861634 | 0.221% | 0.02113 | n | n | PAR15 | intergenic |
| chr7:29662136-29662313 | 0.179% | 0.08897 | y | n | GIPR | intergenic |
| chr19:46189232-46189371 | 0.171% | 0.09034 | n | n | NEUROG3 | downstream |
| chr10:71330866-71331005 | 0.095% | 0.24740 | n | n | COMMD1 | intergenic |
| chr2:62391864-62392042 | 0.147% | 0.54640 | y | n | CDC25C | intron |
| chr5:137673092-137673271 | 0.315% | 1.00000 | y | n | KLHL29 | intron |
| chr2:23925597-23925776 | 0.132% | 1.00000 | y | n | EPB41L3 | intron |
| chr18:54476513-5447812 | 0.128% | 1.00000 | y | y | RAPGEF4 | exon |
| chr2:173883408-173883572 | 0.106% | 1.00000 | y | n | CACTIN | intron |
| chr19:36259953-36261629 | 0.094% | 1.00000 | y | n | GLT8D2 | intron |
| chr12:104444523-104444268 | 0.085% | 1.00000 | | | | |

Figure 10B

| amplicon_location | treated_indel_freq | bonferroni_p value | genic | coding | gene | location |
|---|---|---|---|---|---|---|
| chr2:60722337-60722476 | 74.09% | 0.00000 | | | | |
| chr8:120868614-120868752 | 10.36% | 0.00000 | n | n | DSCC1 | upstream |
| chr2:62391864-62392042 | 1.13% | 0.00000 | n | n | COMMD1 | intergenic |
| chr6:53670690-53670868 | 0.65% | 0.00000 | y | n | LRRC1 | intron |
| chr2:23925597-23925775 | 0.58% | 0.00000 | y | n | KLHL29 | intron |
| chr10:134468242-134468405 | 0.52% | 0.00000 | y | n | INPP5A | intron |
| chr1:54972398-54972568 | 0.51% | 0.00000 | n | n | ACOT11 | upstream |
| chr10:71330866-71331005 | 0.49% | 0.00000 | n | n | NEUROG3 | downstream |
| chr20:36335775-36335954 | 0.38% | 0.11110 | n | n | CTNNBL1 | intron |
| chr14:134048679-134048858 | 0.35% | 0.00000 | y | n | MOSPD1 | intron |
| chr14:67888671-67888848 | 0.30% | 0.00000 | y | n | | intergenic |
| chr13:76123402-76123581 | 0.29% | 0.00000 | y | n | COMMD6 | exon 1 |
| chr11:102556535-102556674 | 0.27% | 0.00000 | n | n | MMP27 | upstream |
| MULTIPLE_TIED_LOCI | 0.26% | 0.00000 | | | | |
| MULTIPLE_TIED_LOCI | 0.22% | 0.00000 | | | | |
| chr11:33915930-33916106 | 0.22% | 0.00000 | n | n | LMO2 | upstream |
| chrX:30298492-30298671 | 0.20% | 0.00372 | n | n | MAGEB1 | intergenic |
| chr17:27181433-27181606 | 0.18% | 0.00206 | n | n | ERAL1 | upstream |
| chr1:29508603-29508766 | 0.16% | 1.00000 | n | n | SRSF4 | upstream |
| chr12:104442523-104442688 | 0.11% | 0.00077 | y | n | GLT8D2 | intron |
| chr19:45909865-45910028 | 0.11% | 1.00000 | y | n | CD3EAP | exon 1 |

SEQUENCE LISTING

<160> NUMBER OF SEQ ID NOS: 38

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaagcaactg ttagcttgca ctagacta                                              28

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Gln Ser Asn Leu Arg Ala
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Pro Tyr Thr Leu Arg Leu
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Gly Tyr Asn Leu Glu Asn
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ser Gly Ser Leu Thr Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Gln Cys Cys Leu Phe His
1               5

<210> SEQ ID NO 7
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 7

Ser Thr Gly Asn Leu Thr Asn
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Arg Gly Ala Leu Lys Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Asn Phe Ser Leu Thr Met
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Asn Gly Asn Leu Arg Asn
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Ser Tyr Asn Leu Ala Asn
1               5

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cacaggctcc aggaagggtt tggcctct                                           28
```

```
<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Asp His Leu Thr Gln
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Gly His Leu Ala Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Lys Gly Thr Leu Gly Glu
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ser Ser Asp Leu Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Asp Asn Leu His Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 18

Arg His Arg Asp Leu Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Asn Asp His Arg Thr Thr
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Lys Ala His Leu Ile Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Gly Arg Asp Leu Ser Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Arg Ala His Leu Thr Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

His Arg Asn Thr Leu Val Arg
1               5
```

```
<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ser Gly Thr Arg Asn His
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Lys Arg Thr Leu Lys Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ser Ser Asn Leu Thr Asn
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ser Ser Asn Leu Gly Asn
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Arg Ser Ala Leu Arg Val
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 29

Arg Ser Arg Asp Leu Thr Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Arg Gln Thr Arg Ala Arg
1               5

<210> SEQ ID NO 31
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His Thr Lys Ile His Leu Arg Gly Ser Gln Leu Val Lys Ser Lys Ser
1               5                   10                  15

Glu Ala Ala Ala Arg Glu Leu Glu Glu Lys
            20                  25

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Thr Lys Ile His Leu Arg Gly Ser Ile Ser Arg Ala Arg Pro Leu
1               5                   10                  15

Asn Pro His Pro Glu Leu Glu Glu Lys
            20                  25

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Thr Lys Ile His Leu Arg Gly Ser Ile Ser Arg Ala Arg Pro Leu
1               5                   10                  15

Asn Pro His Pro Glu Leu Glu Glu Lys
            20                  25

<210> SEQ ID NO 34
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 34

His Thr Lys Ile His Leu Arg Gly Ser Tyr Ala Pro Met Pro Pro Leu
1               5                   10                  15

Ala Leu Ala Ser Pro Glu Leu Glu Glu Lys
                20                  25

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(24)
<223> OTHER INFORMATION: a, c, t, g, unknown or other

<400> SEQUENCE: 35
acacgacgct cttccgatct nnnnagtcct cttctacccc acc              43

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gacgtgtgct cttccgatct ctactcttag acataacaca cc               42

<210> SEQ ID NO 37
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (68)..(72)
<223> OTHER INFORMATION: a, c, t, g, unknown or other

<400> SEQUENCE: 37
nnnnagtagt gtgtgcccgt ctgttgtgtg actctggtaa ctagagatcc ctcagaccct    60
tttagtcnnn nnagtgtgga aaatctctag cag                                93

<210> SEQ ID NO 38
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (26)..(30)
<223> OTHER INFORMATION: a, c, t, g, unknown or other
```

```
<400> SEQUENCE: 38
nnnnctgcta gagattttcc acactnnnnn gactaaaagg gtctgaggga tctctagtta    60
ccagagtcac acaacagacg ggcacacact act                                 93
```

NUCLEASE-MEDIATED REGULATION OF GENE EXPRESSION

CROSS-REFERENCE TO RELATED APPLICATIONS

This application is a 35 U.S.C. § 371 filing of PCT/US2016/032049, filed May 12, 2016, which claims the benefit of U.S. Provisional Application No. 62/160,396, filed May 12, 2015 and U.S. Provisional Application No. 62/303,595, filed Mar. 4, 2016, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Oct. 9, 2017, is named 8328013140_SL.txt and is 9,647 bytes in size.

TECHNICAL FIELD

The present disclosure is in the field of genome engineering, particularly targeted modification of the genome of a hematopoietic cell.

BACKGROUND

When one considers that genome sequencing efforts have revealed that the human genome contains between 20,000 and 25,000 genes, but fewer than 2000 transcriptional regulators, it becomes clear that a number of factors must interact to control gene expression in all its various temporal, developmental and tissue specific manifestations. Expression of genes is controlled by a highly complex mixture of general and specific transcriptional regulators and expression can also be controlled by cis-acting DNA elements. These DNA elements comprise both local DNA elements such as the core promoter and its associated transcription factor binding sites as well as distal elements such as enhancers, silencers, insulators and locus control regions (LCRs) (see Matson et al (2006) *Ann Rev Genome Hum Genet* 7: 29-59).

Enhancer elements were first identified in the SV40 viral genome, and then found in the human immunoglobulin heavy chain locus. Now known to play regulatory roles in the expression of many genes, enhancers appear to mainly influence temporal and spatial patterns of gene expression. It has also been found that enhancers function in a manner that is not dependent upon distance from the core promoter of a gene, and is not dependent on any specific sequence orientation with respect to the promoter. Enhancers can be located several hundred kilobases upstream or downstream of a core promoter region, where they can be located in an intron sequence, or even beyond the 3' end of a gene.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130196373; 20150056705 and 20150335708, the disclosures of which are incorporated by reference in their entireties.

These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). This technique can also be used to introduce site specific changes in the genome sequence through use of a donor oligonucleotide, including the introduction of specific deletions of genomic regions, or of specific point mutations or localized alterations (also known as gene correction). Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. Further, targeted nucleases are being developed based on the Argonaute system (e.g., from *T. thermophilus*, known as 'TtAgo', see Swarts et al (2014) *Nature* 507(7491): 258-261), which also may have the potential for uses in genome editing and gene therapy.

Red blood cells (RBCs), or erythrocytes, are the major cellular component of blood. In fact, RBCs account for one quarter of the cells in a human. Mature RBCs lack a nucleus and many other organelles in humans, and are full of hemoglobin, a metalloprotein that functions to carry oxygen to the tissues as well as carry carbon dioxide out of the tissues and back to the lungs for removal. This protein makes up approximately 97% of the dry weight of RBCs and it increases the oxygen carrying ability of blood by about seventy fold. Hemoglobin is a heterotetramer comprising two alpha ($\alpha$)-like globin chains and two beta ($\beta$)-like globin chains and 4 heme groups. In adults the $\alpha 2\beta 2$ tetramer is referred to as Hemoglobin A (HbA) or adult hemoglobin. Typically, the alpha and beta globin chains are synthesized in an approximate 1:1 ratio and this ratio seems to be critical in terms of hemoglobin and RBC stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. There are two genes that encode fetal globin that are very similar in sequence and are termed HPG1 (also referred to as Ggamma) and HPG2 (Agamma). Fetal hemoglobin protein also contains two $\alpha$ globin chains, but in place of the adult $\beta$-globin chains, it has two fetal gamma ($\gamma$)-globin chains (i.e., fetal hemoglobin is $\alpha 2\gamma 2$). At approximately 30 weeks of gestation, the synthesis of gamma globin in the fetus starts to drop while the production of beta globin increases. By approximately 10 months of age, the newborn's hemoglobin is nearly all $\alpha 2\beta 2$ although some HbF persists into adulthood (approximately 1-3% of total hemoglobin). The regulation of the switch from production of gamma- to beta-globin is quite complex, and primarily involves a down-regulation of gamma globin transcription with a simultaneous up-regulation of beta globin transcription.

Genetic defects in the sequences encoding the hemoglobin chains can be responsible for a number of diseases known as hemoglobinopathies, including sickle cell anemia and thalassemias. In the majority of patients with hemoglobinopathies, the genes encoding gamma globin remain present, but expression is relatively low due to normal gene repression occurring around parturition as described above.

It is estimated that 1 in 5000 people in the U.S. have sickle cell disease (SCD), mostly in people of sub-Saharan Africa descent. There appears to be a benefit for heterozygous carriers of the sickle cell mutation for protection against malaria, so this trait may have been positively selected over time, such that it is estimated that in sub-Saharan Africa, one third of the population has the sickle cell trait. Sickle cell disease is caused by a mutation in the β globin gene as a consequence of which valine is substituted for glutamic acid at amino acid #6 (a GAG to GTG at the DNA level), where the resultant hemoglobin is referred to as "hemoglobinS" or "HbS." Under lower oxygen conditions, a conformational shift in the deoxy form of HbS exposes a hydrophobic patch on the protein between the E and F helices. The hydrophobic residues of the valine at position 6 of the beta chain in hemoglobin are able to associate with the hydrophobic patch, causing HbS molecules to aggregate and form fibrous precipitates. These aggregates in turn cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias are also diseases relating to hemoglobin and typically involve a reduced expression of globin chains. This can occur through mutations in the regulatory regions of the genes or from a mutation in a globin coding sequence that results in reduced expression or reduced levels or functional globin protein. Alpha thalassemias are mainly associated with people of Western Africa and South Asian descent, and may confer malarial resistance. Beta thalassemia is mainly associated with people of Mediterranean descent, typically from Greece and the coastal areas of Turkey and Italy. In thalassemia minor, only one of the β globin alleles bears a mutation. Individuals will suffer from microcytic anemia, and detection usually involves lower than normal mean corpuscular volume (<80 fL). The alleles of subjects with thalassemia minor are β+/β or β0/β (where 'β+' refers to alleles that allow some amount of β chain formation to occur, 'β' refers to wild type β globin alleles, and 'β0' refers to β globin mutations comprising some form of deletion). Thalassemia intermedia subject can often manage a normal life but may need occasional transfusions, especially at times of illness or pregnancy, depending on the severity of their anemia. These patients alleles can be β+/β+ or βo/β+. Thalassemia major occurs when both alleles have thalassemia mutations. This is severely microcytic and hypochromic anemia. Untreated, it causes anemia, splenomegaly and severe bone deformities. It progresses to death before age 20. Treatment consists of periodic blood transfusion; splenectomy for splenomegaly and chelation of transfusion-caused iron overload. Bone marrow transplants are also being used for treatment of people with severe thalassemias if an appropriate donor can be identified, but this procedure can have significant risks.

One approach that has been proposed for the treatment of both SCD and beta thalassemias is to increase the expression of gamma globin with the aim to have HbF functionally replace the aberrant adult hemoglobin. As mentioned above, treatment of SCD patients with hydroxyurea is thought to be successful in part due to its effect on increasing gamma globin expression. The first group of compounds discovered to affect gamma globin reactivation activity were cytotoxic drugs. The ability to cause de novo synthesis of gamma-globin by pharmacological manipulation was first shown using 5-azacytidine in experimental animals (DeSimone (1982) *Proc Nat'l Acad Sci USA* 79(14):4428-31). Subsequent studies confirmed the ability of 5-azacytidine to increase HbF in patients with β-thalassemia and sickle cell disease (Ley, et al., (1982) *N. Engl. J. Medicine,* 307: 1469-1475, and Ley, et al., (1983) *Blood* 62: 370-380). In addition, short chain fatty acids (e.g. butyrate and derivatives) have been shown in experimental systems to increase HbF (Constantoulakis et al., (1988) *Blood* 72(6):1961-1967). Also, there is a segment of the human population with a condition known as 'Hereditary Persistence of Fetal Hemoglobin' (HPFH) where elevated amounts of HbF persist in adulthood (10-40% in HPFH heterozygotes (see Thein et al (2009) *Hum. Mol. Genet* 18 (R2): R216-R223). This is a rare condition, but in the absence of any associated beta globin abnormalities, is not associated with any significant clinical manifestations, even when 100% of the individual's hemoglobin is HbF. When individuals that have a beta thalassemia also have co-incident HPFH, the expression of HbF can lessen the severity of the disease. Further, the severity of the natural course of sickle cell disease can vary significantly from patient to patient, and this variability, in part, can be traced to the fact that some individuals with milder disease express higher levels of HbF.

One approach to increase the expression of HbF involves identification of genes whose products play a role in the regulation of gamma globin expression. One such gene is BCL11A, first identified because of its role in lymphocyte development. BCL11A encodes a zinc finger protein that is thought to be involved in the developmental stage-specific regulation of gamma globin expression. BCL11A is expressed in adult erythroid precursor cells and down-regulation of its expression leads to an increase in gamma globin expression. In addition, it appears that the splicing of the BCL11A mRNA is developmentally regulated. In embryonic cells, it appears that the shorter BCL11A mRNA variants, known as BCL11A-S and BCL11A-XS are primary expressed, while in adult cells, the longer BCL11A-L and BCL11A-XL mRNA variants are predominantly expressed. See, Sankaran et al (2008) *Science* 322 p. 1839. The BCL11A protein appears to interact with the beta globin locus to alter its conformation and thus its expression at different developmental stages. Use of an inhibitory RNA targeted to the BCL11A gene has been proposed (see, e.g., U.S. Patent Publication 20110182867) but this technology has several potential drawbacks, namely that complete knock down may not be achieved, delivery of such RNAs may be problematic and the RNAs must be present continuously, requiring multiple treatments for life.

Targeting of BCL11A enhancer sequences provides a mechanism for increasing HbF. See, e.g., U.S. Patent Publication No. 20150132269. Genome wide association studies have identified a set of genetic variations at BCL11A that are associated with increased HbF levels. These variations are a collection of SNPs found in non-coding regions of BCL11A that function as a stage-specific, lineage-restricted enhancer region. Further investigation revealed that this BCL11A enhancer is required in erythroid cells for BCL11A expression, but is not required for its expression in B cells (see Bauer et al, (2013) *Science* 342:253-257). The enhancer region was found within intron 2 of the BCL11A gene, and three areas of DNAseI hypersensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer 2013, ibid).

Thus, there remains a need for additional methods and compositions that for the alteration of BCL11A gene expression for example to treat hemoglobinopathies such as sickle cell disease and beta thalassemia.

SUMMARY

The present invention describes compositions and methods for use in gene therapy and genome engineering. Specifically, the methods and compositions described relate to inactivating (e.g., by completely or partially abolishing its expression) a BCL11A gene, for example a gene that acts as regulator of one or more additional genes. In particular, the invention describes methods and compositions for interfering with enhancer function in a BCL11A gene to diminish or knock out its activity in specific cell lineages. Additionally, the invention provides methods and compositions for interfering with BCL11A enhancer functions wherein the enhancer sequences are not located within the BCL11A gene. The resulting down-regulation of the BCL11A gene in these circumstances in turn results in increased expression of gamma globin.

In some aspects, the invention comprises a non-naturally occurring zinc finger protein comprising a zinc finger protein (ZFP) comprising 4, 5 or 6 fingers, each finger comprising a recognition helix region that recognizes a target subsite wherein the recognition helix regions comprise the sequences in the order shown in a single row of Table 1. In certain embodiments, the ZFP comprises the recognition helixes as shown in Table 1 for the proteins designated as follows: 51446, 51463, 51484, 51856, 51857 or 51862 (which bind to the target site shown in SEQ ID NO:1) and 51536, 51949, 51990, 51993, 51979, 51982, 52015, 52032 (which bind to the target site shown in SEQ ID NO: 12). Thus, in certain embodiments, provided herein is a zinc finger protein including the following recognition helix regions:

(i)
F1:
(SEQ ID NO: 7)
STGNLTN;

F2:
(SEQ ID NO: 5)
TSGSLTR;

F3:
(SEQ ID NO: 2)
DQSNLRA;
and

F4:
(SEQ ID NO: 6)
AQCCLFH;
or (ii)
F1:
(SEQ ID NO: 2)
DQSNLRA;

F2:
(SEQ ID NO: 3)
RPYTLRL;

F3:
(SEQ ID NO: 8)
SRGALKT;

F4:
(SEQ ID NO: 5)
TSGSLTR;

F5:
(SEQ ID NO: 2)
DQSNLRA;
and

F6:
(SEQ ID NO: 6)
AQCCLFH;

(iii)
F1:
(SEQ ID NO: 2)
DQSNLRA;

F2:
(SEQ ID NO: 9)
RNFSLTM;

F3:
(SEQ ID NO: 10)
SNGNLRN
or
(SEQ ID NO: 7)
STGNLTN
or
(SEQ ID NO: 11)
SSYNLAN;

F4:
(SEQ ID NO: 5)
TSGSLTR;

F5:
(SEQ ID NO: 2)
DQSNLRA;
and

F6:
(SEQ ID NO: 6)
AQCCLFH;
or (iv)
F1:
(SEQ ID NO: 13)
RSDHLTQ;

F2:
(SEQ ID NO: 14)
QSGHLAR;

F3:
(SEQ ID NO: 15)
QKGTLGE;

-continued

F4: RHRDLSR; and (SEQ ID NO: 18)

F5: RRDNLHS; or (SEQ ID NO: 17)

(v)
F1: RNDHRTT; (SEQ ID NO: 19)

F2: QKAHLIR; (SEQ ID NO: 20)

F3: QKGTLGE; (SEQ ID NO: 15)

F4: RGRDLSR or (SEQ ID NO: 21)

LKRTLKR; and (SEQ ID NO: 25)

F5: RRDNLHS; or (SEQ ID NO: 17)

(vi)
F1: RSDHLTQ; (SEQ ID NO: 13)

F2: QRAHLTR; (SEQ ID NO: 22)

F3: QKGTLGE or (SEQ ID NO: 15)

QSGTRNH; (SEQ ID NO: 24)

F4: HRNTLVR; and (SEQ ID NO: 23)

F5: RRDNLHS; or (SEQ ID NO: 17)

(vii)
F1: RSDHLTQ; (SEQ ID NO: 13)

F2: QKAHLIR; (SEQ ID NO: 20)

F3: QKGTLGE or (SEQ ID NO: 15)

QSGTRNH; (SEQ ID NO: 24)

-continued

F4: RGRDLSR; and (SEQ ID NO: 21)

F5: RRDNLHS; or (SEQ ID NO: 17)

(viii)
F1: F1: RSDHLTQ; (SEQ ID NO: 13)

F2: QSGHLAR; (SEQ ID NO: 14)

F3: QSGTRNH; (SEQ ID NO: 24)

F4: QSSDLSR; and (SEQ ID NO: 16)

F5: RRDNLHS. (SEQ ID NO: 17)

In certain embodiments, the zinc finger proteins as described herein are fused to a functional domain (e.g., transcriptional activation domain, transcriptional repression domain, cleavage domain (to form a zinc finger nuclease), etc.). Zinc finger nucleases may be used in dimerizing pairs to cleave at or near one or both of the target sites for the ZFNs of the pair, for example "left partners" of Table 1 (e.g., 51446, 51463, 51484, 51856, 51857, or 51862) can form dimers with the "right partners" of Table 1 (e.g., 51536, 51949, 51990, 51993, 51979, 51982, 52015, or 52032) to cleave BCL11A enhancer sequences.

In another aspect, the invention comprises delivery of at least one nuclease (e.g., a nuclease that binds to a BCL11A enhancer sequence) to a human stem cell or precursor cell (HSC/PC) for the purpose of genome engineering. In certain embodiments, the nuclease comprises a zinc finger protein (ZFP) comprising 4, 5 or 6 fingers, each finger comprising a recognition helix region that recognizes a target subsite wherein the recognition helix regions comprise the sequences in the order shown in a single row of Table 1. The nuclease(s) as described herein may further comprise a linker (e.g., between the DNA-binding domain and the cleavage domain), for example a linker as shown in SEQ ID NOs:26-29 and U.S. Patent Publication No. 20150132269.

In some embodiments, the nuclease is delivered as a peptide, while in others it is delivered as a nucleic acid encoding the at least one nuclease. In some embodiments, more than one nuclease is used. In some preferred embodiments, the nucleic acid encoding the nuclease is an mRNA, and in some instances, the mRNA is protected. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 2012/0195936). In a preferred embodiment, the nucleic acid encoding the nuclease(s) is delivered to the HSC/PC via electroporation. In some embodiments, the nuclease cleaves at or near the binding site of transcription factor. In some aspects, the transcription factor is GATA-1.

In other aspects, the invention comprises a cell or cell line in which an endogenous BCL11A enhancer sequence is genetically modified by a nuclease as described herein (e.g., shown in Table 1), for example as compared to the wild-type sequence of the cell. Nuclease-modified cells or cell lines as described herein are distinguishable in structure and/or function from both wild-type and other modified (nuclease-mediated) cells. The genetically modified cell or cell lines may be heterozygous or homozygous for the modification. The modifications may comprise insertions (e.g., transgene insertion), deletions and/or combinations thereof. In some preferred embodiments, the insertions, deletions and/or combinations thereof result in the destruction of a transcription factor binding site. In certain embodiments, the modification is at or near the nuclease(s) binding and/or cleavage site(s), for example, within 1-300 (or any value therebetween) base pairs upstream or downstream of the site(s) of cleavage, more preferably within 1-100 base pairs (or any value therebetween) of either side of the binding and/or cleavage site(s) shown in Table 1, even more preferably within 1 to 50 base pairs (or any value therebetween) on either side of the binding and/or cleavage site(s). The modification may also include modifications to one or more nucleotides in the cleavage and/or in one or more of the binding sites. In certain embodiments, one or more of the nuclease target site(s) is(are) not modified. In other embodiments, at least one of the target sites for the nuclease(s) is(are) modified. In certain embodiments, the modification is at or near the "+58" region of the BCL11A enhancer, for example, at or near a nuclease binding site shown in any of SEQ ID NO: 1 and SEQ ID NO: 12. Any cell or cell line may be modified by the nucleases as described herein, for example a stem cell (hematopoietic stem cell such as a CD34+ hematopoietic stem cell) or red blood cell (RBC) precursor cell. Also described are cells or cell lines obtained following modification by a nuclease as described herein, for example cells or cell lines descended from a nuclease-modified cell or cell line. Partially or fully differentiated cells descended from the modified stem cells as described herein are also provided (e.g., RBCs or RBC precursor cells). The cells descended from the nuclease-modified cells may be propagated (and/or differentiated) in vitro (culture) or may differentiate within a live subject, for example following ex vivo administration of a nuclease-modified stem cell. Any of the genetically modified cells or cell lines disclosed herein may show increased expression of gamma globin. Compositions such as pharmaceutical compositions comprising the genetically modified cells as described herein are also provided.

In other aspects, the invention comprises delivery of a donor nucleic acid to a target cell to provide a genetically modified cell in which the donor is integrated into the cell. The donor may be delivered prior to, after, or along with the nucleic acid encoding the nuclease(s) of Table 1. The donor nucleic acid may comprise an exogenous sequence (transgene) to be integrated into the genome of the cell, for example, an endogenous locus. In some embodiments, the donor may comprise a full length gene or fragment thereof flanked by regions of homology with the targeted cleavage site. In some embodiments, the donor lacks homologous regions and is integrated into a target locus through homology independent mechanism (i.e. NHEJ). The donor may comprise any nucleic acid sequence, for example a nucleic acid that, when used as a substrate for homology-directed repair of the nuclease-induced double-strand break, leads to a donor-specified deletion to be generated at the endogenous chromosomal locus (e.g., BCL11A enhancer region) or, alternatively (or in addition to), novel allelic forms of (e.g., point mutations that ablate a transcription factor binding site) the endogenous locus to be created. In some aspects, the donor nucleic acid is an oligonucleotide wherein integration leads to a gene correction event, or a targeted deletion.

In other aspects, the nuclease and/or donor is(are) delivered by viral and/or non-viral gene transfer methods. In preferred embodiments, the donor is delivered to the cell via an adeno-associated virus (AAV). In some instances, the AAV comprises LTRs that are of a heterologous serotype in comparison with the capsid serotype.

In some aspects, deletions comprising regions within the DNAseI hypersensitive regions of the enhancer (e.g., the +58 region of the BCL11A enhancer) are made using one or more nucleases as shown in Table 1. These deletions can comprise from about 1 nucleotide to about 551 nucleotides. Thus, the deletions can comprise, 1, 5, 10, 15, 20, 25, 30, 40, 50, 100, 150, 200, 250, 300, 350, 400, 450, 500, 550 nucleotides, or any value therebetween. In some embodiments, the deletions comprise binding regions for one or more transcription factors. In some preferred embodiments, the deletions comprise a GATA-1 binding site, or the binding site for GATA-1 in combination with other factors.

In some embodiments, the DNA binding domains of Table 1 are fused to a functional domain. Some aspects include fusion of the DNA binding domains with domains capable of regulating the expression of a gene. In some embodiments, the fusion proteins comprise the DNA binding domain of Table 1 fused to a gene expression modulatory domain where the modulator represses gene expression.

In some embodiments, the HSC/PC cells are contacted with the nucleases and/or DNA binding proteins of the invention (i.e., ZFPs as shown in Table 1). In some embodiments, the nucleases and/or DNA binding proteins are delivered as nucleic acids and in other embodiments, they are delivered as proteins. In some embodiments, the nucleic acids are mRNAs encoding the nucleases and/or DNA binding proteins, and in further embodiments, the mRNAs may be protected. In some embodiments, the mRNA may be chemically modified, may comprise an ARCA cap and/or may comprise a mixture of unmodified and modified nucleotides. Cells or cell lines descended from these cells are also provided, including partially or fully differentiated cells.

In some aspects, the HSC/PC are contacted with the nucleases and/or DNA binding proteins of the invention ex vivo, following apheresis of the HSC/PC from a subject, or purification from harvested bone marrow. In some embodiments, the nucleases described herein cause modifications within the BCL11A enhancer regions, for example resulting a genetically modified cell that is structurally and/or functionally distinct from wild-type and/or other modified (e.g., nuclease-modified) cells. In further embodiments, the HSC/PC containing the BCL11A enhancer region modifications are introduced back into the subject. In some instances, the HSC/PC containing the BCL11A enhancer region modifications are expanded prior to introduction. In other aspects, the genetically modified HSC/PCs are given to the subject in a bone marrow transplant wherein the HSC/PC engraft, differentiate and mature in vivo. In some embodiments, the HSC/PC are isolated from the subject following G-CSF- and/or plerixafor-induced mobilization, and in others, the cells are isolated from human bone marrow or human umbilical cords. In some aspects, the subject is treated to a mild myeloablative procedure prior to introduction of the graft comprising the modified HSC/PC, while in other aspects, the subject is treated with a vigorous myeloablative conditioning regimen. In some embodiments, the methods and compositions of the invention are used to treat or prevent a hemoglobinopathy. In some aspects, the hemoglobinopathy is a beta thalassemia, while in other aspects, the hemoglobinopathy is sickle cell disease.

In some embodiments, the HSC/PC are further contacted with a donor molecule. In some embodiments, the donor molecule is delivered by a viral vector. The donor molecule may comprise one or more sequences encoding a functional polypeptide (e.g., a cDNA or fragment thereof), with or without a promoter. Additional sequences (coding or non-coding sequences) may be included when a donor molecule is used for inactivation, including but not limited to, sequences encoding a 2A peptide, SA site, IRES, etc.

In one aspect, the methods and compositions of the invention comprise methods for contacting the HSC/PC in vivo. The nucleases and/or DNA binding proteins are delivered to HSC/PC in situ by methods known in the art. In some embodiments, the nucleases and/or DNA binding proteins of the invention comprise a viral particle that is administered to the subject in need, while in others, the nucleases and/or DNA binding proteins comprise a nanoparticle (e.g. liposome). In some embodiments, the viral particles and/or nanoparticles are delivered to the organ (e.g. bone marrow) wherein the HSC/PC reside.

In another aspect, described herein are methods of integrating a donor nucleic acid into the genome of a cell via homology-independent mechanisms. The methods comprise creating a double-stranded break (DSB) in the genome of a cell and cleaving the donor molecule using a nuclease as described herein, such that the donor nucleic acid is integrated at the site of the DSB. In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism. In certain embodiments, the DSB is created by one or more zinc-finger nucleases (ZFNs), fusion proteins comprising a zinc finger binding domain, which is engineered to bind a sequence within the region of interest, and a cleavage domain or a cleavage half-domain.

In one aspect, the donor may encode a regulatory protein of interest (e.g. ZFP TFs, TALE TFs or a CRISPR/Cas TF) that binds to and/or modulates expression of a gene of interest. In one embodiment, the regulatory proteins bind to a DNA sequence and prevent binding of other regulatory factors. In another embodiment, the binding of the regulatory protein may modulate (i.e. induce or repress) expression of a target DNA.

In some embodiments, the transgenic HSC/PC cell and/or animal includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

In another aspect, provided herein is a method of altering gene expression (e.g., BCL11A and/or a globin gene) in a cell, the method comprising: introducing, into the cell, one or more nucleases as described herein (shown in Table 1), under conditions such that the one or more proteins are expressed and expression of the gene is altered. In certain embodiments, expression of a globin gene (e.g., gamma globin or beta globin) is altered (e.g., increased). Any of the methods described herein may further comprise integrating a donor sequence (e.g., transgene or fragment thereof under the control of an exogenous or endogenous promoter) into the genome of the cell, for example integrating a donor at or near the site of nuclease cleavage in the BCL11A gene. The donor sequence is introduced to the cell using a viral vector, as an oligonucleotide and/or on a plasmid. The cell in which gene expression is altered may be, for example, a red blood cell (RBC) precursor cell and/or a hematopoietic stem cell (e.g., CD34+ cell).

In other embodiments, provided herein is a method of producing a genetically modified cell comprising a genomic modification within an endogenous BCL11A enhancer sequence (a modification to the nucleotide sequence of the BCL11A enhancer sequence), the method comprising the steps of: a) contacting a cell with a polynucleotide (e.g. DNA or mRNA) encoding a zinc finger nuclease comprising 4, 5, or 6 zinc finger domains in which each of the zinc finger domains comprises a recognition helix region in the order shown in a single row of Table 1; b) subjecting the cell to conditions conducive to expressing the zinc finger protein from the polynucleotide; and c) modifying the endogenous BCL11A enhancer sequence with the expressed zinc finger protein sufficient to produce the genetically modified cell. In certain embodiments, the cells are stimulated with at least one cytokine (e.g., prior to step (a)). The polynucleotide may be contacted with the cell using any suitable method, including but not limited, via transfection, using a non-viral vector, using a viral vector, by chemical means or by exposure to an electric field (e.g., electroporation).

Cells comprising one or a combination of the genomic modifications described herein are also provided, including cells descended from the cells produced by the methods described herein.

Also provided is a method of treating a patient in need of an increase in globin gene expression, the method comprising administering to the patient the pharmaceutical preparation (genetically modified cells, proteins and/or polynucleotides) as described herein in an amount sufficient to increase the globin gene expression in the patient. In certain embodiments, the patient is known to have, is suspected of having, or is at risk of developing a thalassemia or sickle cell disease.

A kit, comprising the nucleic acids, proteins and/or genetically modified cells of the invention, is also provided. The kit may comprise nucleic acids encoding the nucleases, (e.g. RNA molecules or ZFN, TALEN or CRISPR/Cas system encoding genes contained in a suitable expression vector), or aliquots of the nuclease proteins, donor molecules, suitable stemness modifiers, cells, buffers, and/or instructions (e.g., for performing the methods of the invention) and the like. The invention includes, but is not limited to, a genetically modified cell (e.g., stem cell such as a hematopoietic (CD34+) stem cell or RBC precursor cell) comprising at least one genomic modification made by a nuclease (e.g., as shown in a single row of Table 1), wherein the genomic modification is within an endogenous BCL11A enhancer sequence, and further wherein the genomic modification is selected from the group consisting of insertions, deletions and combinations thereof and comprises a modification at or near any of SEQ ID NO: 1 and SEQ ID NO: 12. In certain embodiments, the cell is a genetically modified differentiated cell descended from a stem cell as described herein (e.g., a RBC descended from a hematopoietic stem cell or RBC precursor cell).

The nuclease may comprise at least one zinc finger nuclease (ZFN) (e.g., as shown in Table 1) and/or at least one TALEN and the nuclease(s) may be introduced into the cell in protein form and/or as a polynucleotide encoding the nuclease(s). In certain embodiments, the genomic modification comprises an insertion that comprises integration of a donor polynucleotide encoding a transgene. Also provided are pharmaceutical compositions comprising one or more of the genetically modified cells as described herein.

Also provided is a DNA-binding protein comprising a zinc finger protein comprising 4, 5 or 6 zinc finger domains comprising a recognition helix region, wherein the zinc finger proteins comprise the recognition helix regions in the order shown in a single row of Table 1. Also provided is a TALE protein comprising a plurality of repeats that bind to a sequence comprising a portion (e.g., at least 4, 5, 6 or more) base pairs of the target sites shown in Table 1. A fusion protein comprising a zinc finger protein or TALE protein as described herein and a wild-type or engineered cleavage domain or cleavage half-domain is also provided as are polynucleotides encoding the proteins (ZFPs, TALEs, ZFNs, TALENs) as described herein. Cells (e.g., isolated stem cells such as hematopoietic (CD34+) stem cells) comprising one or more polynucleotides and/or proteins as described herein are also provided. Also provided are kits comprising one or more proteins, polynucleotides and/or cells as described herein.

A method of altering globin gene expression in a cell (e.g., RBC precursor cell and/or hematopoietic stem cell) is also described, the method comprising: introducing, into the cell, one or more polynucleotides encoding one or more nucleases as described herein, under conditions such that the one or more proteins are expressed and expression of the globin gene (e.g., gamma and/or beta globin) is altered (e.g., increased). In certain embodiments, the methods further comprise integrating a donor sequence into the genome of the cell, for example using a viral vector, as an oligonucleotide or on a plasmid. The donor sequence may comprise a transgene under the control of an endogenous or exogenous promoter.

Also provided is a method of producing a genetically modified cell comprising a genomic modification within an endogenous BCL11A enhancer sequence (e.g., target site as shown in Table 1), the method comprising the steps of: (a) contacting a cell with a polynucleotide encoding a fusion protein comprising a zinc finger nuclease comprising 4, 5, or 6 zinc finger domains in which each of the zinc finger domains comprises a recognition helix region in the order shown in a single row of Table 1; (b) subjecting the cell to conditions conducive to expressing the fusion protein from the polynucleotide; and (c) modifying the endogenous BCL11A enhancer sequence with the expressed fusion protein sufficient to produce the genetically modified cell. In certain embodiments, the method further comprises stimulating the cells with at least one cytokine. The polynucleotide(s) may be delivered inside the cell, for example using a non-viral delivery system, a viral delivery system, and/or a delivery vehicle and may comprise subjecting the cells to an electric field.

Methods of treating a patient in need of an increase in globin gene expression (e.g., a patient is known to have, is suspected of having, or is at risk of developing a globinopathy such as a thalassemia (e.g., β-thalassemia) or sickle cell disease are also provided, the method comprising administering to the patient the pharmaceutical composition as described herein (e.g., proteins, polynucleotides and/or cells) in an amount sufficient to increase the globin gene expression in the patient.

These and other aspects will be readily apparent to the skilled artisan in light of disclosure as a whole.

BRIEF DESCRIPTION OF THE DRAWINGS

FIG. 4B depicts the activity of one pair of ZFNs where the ZFNs are supplied either as a single mRNA species with a 2a self-cleaving peptide sequence separating the sequences encoding each ZFN or when the two ZFNs are supplied on separate mRNAs.

FIGS. 5A and 5B depicts activity of ZFN pairs in PB derived CD34+ cells using a Maxcyte electroporation device. The % indels detected (measurement of detectable NHEJ activity) for each condition are shown below the graphs for FIG. 5A and FIG. 5B. FIG. 5A depicts a comparison between two ZFN pairs, and FIG. 5B depicts the activity of the ZFNs pairs when the ZFNs are supplied either as a single mRNA species with a 2a self-cleaving peptide sequence separating the sequences encoding each ZFN or when the two ZFNs are supplied on separate mRNAs.

FIGS. 10A and 10B are tables depicting the results of the off-target analysis for Pair A (FIG. 10A) and Pair B (FIG. 10B).

DETAILED DESCRIPTION

Figure 1:
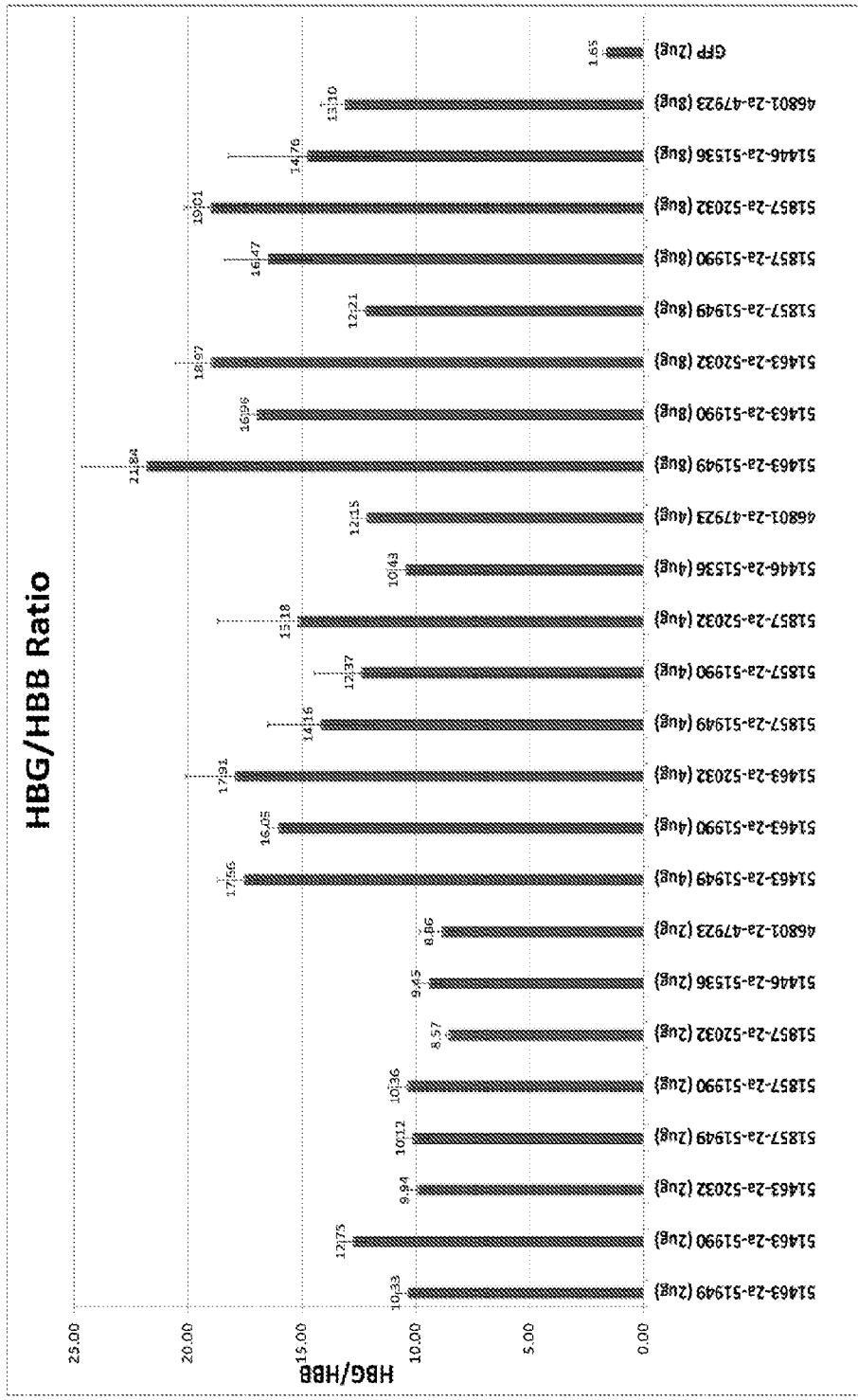
FIG. 1 is a graph depicting the relative ratio of human gamma globin expression (HBG) to human beta globin expression (HBB) in red blood cells derived from CD34+ cells edited with the BCL11a-specific ZFN pairs shown.

Disclosed herein are compositions and methods for genome engineering for the modulation of BCL11A and/or gamma globin expression and for the treatment and/or prevention of hemoglobinopathies. In particular, nucleases comprising the ZFPs having the recognition helix regions as shown in a single row of Table 1 is efficiently achieved in HSC/PC and results in a change in relative gamma globin expression during subsequent erythropoiesis. This modulation of BCL11A and gamma globin expression is particularly useful for treatment of hemoglobinopathies (e.g., beta thalassemias, sickle cell disease) wherein there is insufficient beta globin expression or expression of a mutated form of beta-globin. Using the methods and compositions of the invention, the complications and disease related sequelae caused by the aberrant beta globin can be overcome by alteration of the expression of gamma globin in erythrocyte precursor cells.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units.

The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,586,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g., Swarts et al, ibid, G. Sheng et al., (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and −" cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 20080131962 and 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules.

Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "protected" mRNA is one in which the mRNA has been altered in some manner to increase the stability or translation of the mRNA. Examples of protections include the use of replacement of up to 25% of the cytodine and uridine residues with 2-thiouridine (s2U) and 5-methylcytidine (m5C). The resulting mRNA exhibits less immunogenicity and more stability as compared with its unmodified counterpart. (see Karikó et al. ((2012), *Molecular Therapy*, Vol. 16, No. 11, pages 1833-1844). Other changes include the addition of a so-called ARCA cap, which increases the translationability of the in vitro produced mRNA (see U.S. Pat. No. 7,074,596).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE of Cas DNA-binding domain portion is able to bind its target site and/or its binding site, while the activation domain is able to upregulate gene expression. When a fusion polypeptide in which a ZFP, TALE or Cas DNA-binding domain is fused to a cleavage domain, the ZFP, TALE or Cas DNA-binding domain and the cleavage domain are in operative linkage if, in the fusion polypeptide, the ZFP, TALE or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the or stem cells of the invention can be administered. Subjects of the present invention include those that have been exposed to one or more chemical toxins, including, for example, a nerve toxin.

"Stemness" refers to the relative ability of any cell to act in a stem cell-like manner, i.e., the degree of toti-, pluri-, or oligo-potency and expanded or indefinite self-renewal that any particular stem cell may have.

Nucleases

Described herein are compositions, particularly nucleases, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Domains

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

Nearly any linker (spacer) may be used between one or more of the components of the DNA-binding domain (e.g., zinc fingers), between one or more DNA-binding domains and/or between the DNA-binding domain and the functional domain (e.g., nuclease). Non-limiting examples of suitable linker sequences include U.S. Pat. Nos. 8,772,453; 7,888,121; 6,479,626; 6,903,185; and 7,153,949; and U.S. Publication Nos. 20090305419; 20150064789 and 20150132269. Thus, the proteins described herein may include any combination of suitable linkers between the individual DNA-binding components and/or between the DNA-binding domain and the functional domain of the compositions described herein.

B. Cleavage Domains

Any suitable cleavage domain can be operatively linked to the DNA-binding domains as described herein to form a nuclease. The cleavage domain may be heterologous to the DNA-binding domain, for example a zinc finger DNA-binding domain and a cleavage domain from a nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95:10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. No. 7,888,121 incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in See, e.g., U.S. Pat. Nos. 7,914,796; 8,034,598 and 8,623,618, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively. See, e.g., U.S. Pat. Nos. 7,914,796; 8,034,598 and 8,623,618. In other embodiments, the engineered cleavage half domain comprises the "Sharkey" and/or "Sharkey'" mutations (see Guo et al, (2010)*J. Mol. Biol.* 400(1):96-107).

Engineered cleavage half-domains described herein can be prepared using any suitable method, for example, by site-directed mutagenesis of wild-type cleavage half-domains (Fok I) as described in U.S. Pat. Nos. 7,888,121; 7,914,796; 8,034,598 and 8,623,618.

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Expression of the nuclease may be under the control of a constitutive promoter or an inducible promoter, for example the galactokinase promoter which is activated (de-repressed) in the presence of raffinose and/or galactose and repressed in presence of glucose.

The nuclease(s) as described herein may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) *Nucleic Acids Res.* 44(2):e11. doi: 10.1093/nar/gkv878. Epub 2015 Oct. 19.

Target Sites

As described in detail above, DNA domains can be engineered to bind to any sequence of choice. An engineered DNA-binding domain can have a novel binding specificity, compared to a naturally-occurring DNA-binding domain. In certain embodiments, the DNA-binding domains bind to a sequence within a BCL11A enhancer sequence, for example a target site (typically 9, 10, 11, 12, 13, 14, 15, 16, 17, 18, 19, 20, 21 or even more base pairs) is between exon 2 and exon 3 of BCL11A, including DNA-binding domains that bind to a sequence within a DNAseI hypersensitive site in the BCL11A enhancer sequence (e.g., +58) as shown in Table 1. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) and/or fusions of DNA-binding domain(s) and functional domain(s) may be linked together using any suitable linker sequences, including for example, linkers of 5 or more amino acids. U.S. Pat. Nos. 8,772,453; 7,888,121 (e.g., "ZC" linker); U.S. Pat. Nos. 6,479,626; 6,903,185; and 7,153,949; U.S. Publication No. 20090305419) and 20150064789. The proteins described herein may include any combination of suitable linkers between the individual DNA-binding domains of the protein. See, also, U.S. Pat. No. 8,586,526.

Donors

In certain embodiments, the present disclosure relates to nuclease-mediated targeted integration of an exogenous sequence into the genome of a cell using the BCL11A enhancer region-binding molecules described herein. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms. Additionally, donor sequences can comprise a vector molecule containing sequences that are not homologous to the region of interest in cellular chromatin. A donor molecule can contain several, discontinuous regions of homology to cellular chromatin, and, for example, lead to a deletion of a Bcl11a enhancer region (or a fragment thereof) when used as a substrate for repair of a DBS induced by one of the nucleases described here. Further, for targeted insertion of sequences not normally present in a region of interest, said sequences can be present in a donor nucleic acid molecule and flanked by regions of homology to sequence in the region of interest.

Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Patent Publication Nos. 20100047805 and 20110207221. The donor sequence(s) are preferably contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. If introduced in double-stranded form, the donor may include one or more nuclease target sites, for example, nuclease target sites flanking the transgene to be integrated into the cell's genome. See, e.g., U.S. Patent Publication No. 20130326645.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In other embodiments, the transgene (e.g., with or without globin encoding sequences) is integrated into any endogenous locus, for example a safe-harbor locus. See, e.g., U.S. Patent Publications 20080299580; 20080159996 and 201000218264.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasiaossificans progressive, fragile X syndrome, galactosemis, Gaucher's disease, generalized gangliosidoses (e.g., GM1), hemochromatosis, the hemoglobin C mutation in the 6$^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, *porphyria*, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases as described herein (Table 1), polynucleotides encoding these nucleases, donor polynucleotides and compositions comprising the proteins and/or polynucleotides described herein may be delivered in vivo or ex vivo by any suitable means into any cell type.

Suitable cells include eukaryotic (e.g., animal) and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Agl4, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering nucleases as described herein are described, for example, in U.S. Pat. Nos. 6,453,242; 6,503, 717; 6,534,261; 6,599,692; 6,607,882; 6,689,558; 6,824, 978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the ZFN(s), described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors (DNA MC(s)). When multiple vectors are used, each vector may comprise a sequence encoding one or multiple nucleases and/or donor constructs. Conventional viral and non-viral based gene transfer methods can be used to introduce nucleic acids encoding nucleases and/or donor constructs in cells (e.g., mammalian cells) and target tissues. Non-viral vector delivery systems include DNA or RNA plasmids, DNA MCs, naked nucleic acid, and nucleic acid complexed with a delivery vehicle such as a liposome or poloxamer. Suitable non-viral vectors include nanotaxis vectors, including vectors commercially available from InCellArt (France). Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10): 1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs, TALEs and/or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or double-stranded donors) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/0117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, the nucleases and donors can be carried by the same DNA MC. Alternatively, a donor polynucleotide can be carried by a MC, while the one or more nucleases can be carried by a standard plasmid or AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein. The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.,* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Cells

Also described herein are cells and/or cell lines in which an endogenous BCL11A enhancer sequence is modified by the nucleases described herein (Table 1). The modification may be, for example, as compared to the wild-type sequence of the cell. The cell or cell lines may be heterozygous or homozygous for the modification. The modifications to the BCL11A sequence may comprise insertions, deletions and/or combinations thereof.

The modification is preferably at or near the nuclease(s) binding and/or cleavage site(s), for example, within 1-300 (or any value therebetween) base pairs upstream or downstream of the site(s) of cleavage, more preferably within 1-100 base pairs (or any value therebetween) of either side of the binding and/or cleavage site(s), even more preferably within 1 to 50 base pairs (or any value therebetween) on either side of the binding and/or cleavage site(s). In certain embodiments, the modification is at or near the "+58" region of the BCL11A enhancer, for example, at or near a nuclease binding site shown in any of the first column of Table 1.

Any cell or cell line may be modified, for example a stem cell, for example an embryonic stem cell, an induced pluripotent stem cell, a hematopoietic stem cell, a neuronal stem cell and a mesenchymal stem cell. Other non-limiting examples of cells as described herein include T-cells (e.g., CD4+, CD3+, CD8+, etc.); dendritic cells; B-cells. A descendent of a stem cell, including a partially or fully differentiated cell, is also provided (e.g., a RBC or RBC precursor cell). Non-limiting examples other cell lines including a modified BCL11A sequence include COS, CHO (e.g., CHO-S, CHO-K1, CHO-DG44, CHO-DUXB11, CHO-DUKX, CHOK1SV), VERO, MDCK, W138, V79, B14AF28-G3, BHK, HaK, NSO, SP2/0-Agl4, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*.

The cells as described herein are useful in treating and/or preventing a disorder, for example, by ex vivo therapies. The nuclease-modified cells can be expanded and then reintroduced into the patient using standard techniques. See, e.g., Tebas et al (2014) *New Eng J Med* 370(10):901. In the case of stem cells, after infusion into the subject, in vivo differentiation of these precursors into cells expressing the functional transgene also occurs. Pharmaceutical compositions comprising the cells as described herein are also provided. In addition, the cells may be cryopreserved prior to administration to a patient.

Any of the modified cells or cell lines disclosed herein may show increased expression of gamma globin. Compositions such as pharmaceutical compositions comprising the genetically modified cells as described herein are also provided Applications The methods and compositions disclosed herein are for modifying expression of protein, or correcting an aberrant gene sequence that encodes a protein expressed in a genetic disease, such as a sickle cell disease or a thalassemia. Thus, the methods and compositions provide for the treatment and/or prevention of such genetic diseases. Genome editing, for example of stem cells, can be used to correct an aberrant gene, insert a wild type gene, or change the expression of an endogenous gene. By way of non-limiting example, a wild type gene, e.g. encoding at least one globin (e.g., a and/or β globin), may be inserted into a cell (e.g., into an endogenous BCL11a enhancer sequence using one or more nucleases as described herein) to provide the globin proteins deficient and/or lacking in the cell and thereby treat a genetic disease, e.g., a hemoglobinopathy, caused by faulty globin expression. Alternatively or in addition, genomic editing with or without administration of the appropriate donor, can correct the faulty endogenous gene, e.g., correcting the point mutation in α- or β-hemoglobin, to restore expression of the gene and/or treat a genetic disease, e.g. sickle cell disease and/or knock out or alteration (overexpression or repression) of any direct or indirect globin regulatory gene (e.g. inactivation of the γ globin-regulating gene BCL11A or the BCL11A-regulator KLF1). Specifically, the methods and compositions of the invention have use in the treatment or prevention of hemoglobinopathies.

The nucleases of the invention are targeted to the BCL11A enhancer region, known to be required for the expression of BCL11A, and hence the down regulation of gamma globin expression. Modification of this enhancer region may result in erythrocytes with increased gamma globin expression, and thus may be helpful for the treatment or prevention of sickle cell disease or beta thalassemia.

The following Examples relate to exemplary embodiments of the present disclosure in which the nuclease comprises a zinc finger nuclease (ZFN). It will be appreciated that this is for purposes of exemplification only and that other nucleases can be used, for example TtAgo and CRISPR/Cas systems, homing endonucleases (meganucleases) with engineered DNA-binding domains and/or fusions of naturally occurring of engineered homing endonucleases (meganucleases) DNA-binding domains and heterologous cleavage domains and/or fusions of meganucleases and TALE proteins.

EXAMPLES

Example 1: Assembly of Zinc Finger Nucleases

ZFNs were assembled against the human BCL11A gene and were tested by CEL1 assays as described in Miller et al. (2007) *Nat. Biotechnol.* 25:778-785. ZFNs specific for the +58 region of the enhancer region were made as described. The nucleases are shown below in Table 1:

TABLE 1

ZFN pairs specific for +58 BCL11A enhancer region

| SBS # (target site, 5'-3') | Design | | | | | |
|---|---|---|---|---|---|---|
| | F1 | F2 | F3 | F4 | F5 | F6 |
| Left partner | | | | | | |
| 46801 aaAGCAACtG TTAGCTTGCA Ctagacta (SEQ ID NO: 1) | DQSNLRA (SEQ ID NO: 2) | RPYTLRL (SEQ ID NO: 3) | SGYNLEN (SEQ ID NO: 4) | TSGSLTR (SEQ ID NO: 5) | DQSNLRA (SEQ ID NO: 2) | AQCCLFH (SEQ ID NO: 6) |

TABLE 1-continued

ZFN pairs specific for +58 BCL11A enhancer region

SBS # (target site, 5'-3')

| | Design | | | | | |
|---|---|---|---|---|---|---|
| | F1 | F2 | F3 | F4 | F5 | F6 |
| 51446 aaAGCAACtG TTAGCttgca ctagacta (SEQ ID NO: 1) | STGNLTN (SEQ ID NO: 7) | TSGSLTR (SEQ ID NO: 5) | DQSNLRA (SEQ ID NO: 2) | AQCCLFH (SEQ ID NO: 6) | N/A | N/A |
| 51463 aaAGCAACtG TTAGCttgca ctagacta (SEQ ID NO: 1) | STGNLTN (SEQ ID NO: 7) | TSGSLTR (SEQ ID NO: 5) | DQSNLRA (SEQ ID NO: 2) | AQCCLFH (SEQ ID NO: 6) | N/A | N/A |
| 51484 aaAGCAACtG TTAGCTTGCA Ctagacta (SEQ ID NO: 1) | DQSNLRA (SEQ ID NO: 2) | RPYTLRL (SEQ ID NO: 3) | SRGALKT (SEQ ID NO: 8) | TSGSLTR (SEQ ID NO: 5) | DQSNLRA (SEQ ID NO: 2) | AQCCLFH (SEQ ID NO: 6) |
| 51856 aaAGCAACtG TTAGCTTGCA Ctagacta (SEQ ID NO: 1) | DQSNLRA (SEQ ID NO: 2) | RNFSLTM (SEQ ID NO: 9) | SNGNLRN (SEQ ID NO: 10) | TSGSLTR (SEQ ID NO: 5) | DQSNLRA (SEQ ID NO: 2) | AQCCLFH (SEQ ID NO: 6) |
| 51857 aaAGCAACtG TTAGCTTGCA Ctagacta (SEQ ID NO: 1) | DQSNLRA (SEQ ID NO: 2) | RNFSLTM (SEQ ID NO: 9) | STGNLTN (SEQ ID NO: 7) | TSGSLTR (SEQ ID NO: 5) | DQSNLRA (SEQ ID NO: 2) | AQCCLFH (SEQ ID NO: 6) |
| 51862 aaAGCAACtG TTAGCTTGCA Ctagacta (SEQ ID NO: 1) | DQSNLRA (SEQ ID NO: 2) | RNFSLTM (SEQ ID NO: 9) | SSYNLAN (SEQ ID NO: 11) | TSGSLTR (SEQ ID NO: 5) | DQSNLRA (SEQ ID NO: 2) | AQCCLFH (SEQ ID NO: 6) |
| 51477 aaAGCAACtG TTAGCTTGCA Ctagacta (SEQ ID NO: 1) | DQSNLRA (SEQ ID NO: 2) | RPYTLRL (SEQ ID NO: 3) | SSSNLTN (SEQ ID NO: 26) | TSGSLTR (SEQ ID NO: 5) | DQSNLRA (SEQ ID NO: 2) | AQCCLFH (SEQ ID NO: 6) |
| 51478 aaAGCAACtG TTAGCTTGCA Ctagacta (SEQ ID NO: 1) | DQSNLRA (SEQ ID NO: 2) | RPYTLRL (SEQ ID NO: 3) | SSSNLGN (SEQ ID NO: 27) | TSGSLTR (SEQ ID NO: 5) | DQSNLRA (SEQ ID NO: 2) | AQCCLFH (SEQ ID NO: 6) |
| 51487 aaAGCAACtG TTAGCTTGCA Ctagacta (SEQ ID NO: 1) | DQSNLRA (SEQ ID NO: 2) | RPYTLRL (SEQ ID NO: 3) | SRSALRV (SEQ ID NO: 28) | TSGSLTR (SEQ ID NO: 5) | DQSNLRA (SEQ ID NO: 2) | AQCCLFH (SEQ ID NO: 6) |
| Right Partner | | | | | | |
| 47923 caCAGGCTCC AGGAAGGgtt tggcctct (SEQ ID NO: 12) | RSDHLTQ (SEQ ID NO: 13) | QSGHLAR (SEQ ID NO: 14) | QKGTLGE (SEQ ID NO: 15) | QSSDLSR (SEQ ID NO: 16) | RRDNLHS (SEQ ID NO: 17) | N/A |

TABLE 1-continued

ZFN pairs specific for +58 BCL11A enhancer region

| SBS # (target site, 5'-3') | Design | | | | | |
|---|---|---|---|---|---|---|
| | F1 | F2 | F3 | F4 | F5 | F6 |
| 51536 caCAGGCTCC AGGAAGGgtt tggcctct (SEQ ID NO: 12) | RSDHLTQ (SEQ ID NO: 13) | QSGHLAR (SEQ ID NO: 14) | QKGTLGE (SEQ ID NO: 15) | RHRDLSR (SEQ ID NO: 18) | RRDNLHS (SEQ ID NO: 17) | N/A |
| 51949 caCAGGCTCC AGGAAGGgtt tggcctct (SEQ ID NO: 12) | RNDHRTT (SEQ ID NO: 19) | QKAHLIR (SEQ ID NO: 20) | QKGTLGE (SEQ ID NO: 15) | RGRDLSR (SEQ ID NO: 21) | RRDNLHS (SEQ ID NO: 17) | N/A |
| 51990 caCAGGCTCC AGGAAGGgtt tggcctct (SEQ ID NO: 12) | RSDHLTQ (SEQ ID NO: 13) | QRAHLTR (SEQ ID NO: 22) | QKGTLGE (SEQ ID NO: 15) | HRNTLVR (SEQ ID NO: 23) | RRDNLHS (SEQ ID NO: 17) | N/A |
| 51993 caCAGGCTCC AGGAAGGgtt tggcctct (SEQ ID NO: 12) | RSDHLTQ (SEQ ID NO: 13) | QRAHLTR (SEQ ID NO: 22) | QSGTRNH (SEQ ID NO: 24) | HRNTLVR (SEQ ID NO: 23) | RRDNLHS (SEQ ID NO: 17) | N/A |
| 51979 caCAGGCTCC AGGAAGGgtt tggcctct (SEQ ID NO: 12) | RSDHLTQ (SEQ ID NO: 13) | QKAHLIR (SEQ ID NO: 20) | QKGTLGE (SEQ ID NO: 15) | RGRDLSR (SEQ ID NO: 21) | RRDNLHS (SEQ ID NO: 17) | N/A |
| 51982 caCAGGCTCC AGGAAGGgtt tggcctct (SEQ ID NO: 12) | RSDHLTQ (SEQ ID NO: 13) | QKAHLIR (SEQ ID NO: 20) | QSGTRNH (SEQ ID NO: 24) | RGRDLSR (SEQ ID NO: 21) | RRDNLHS (SEQ ID NO: 17) | N/A |
| 52015 caCAGGCTCC AGGAAGGgtt tggcctct (SEQ ID NO: 12) | RNDHRTT (SEQ ID NO: 19) | QKAHLIR (SEQ ID NO: 20) | QKGTLGE (SEQ ID NO: 15) | LKRTLKR (SEQ ID NO: 25) | RRDNLHS (SEQ ID NO: 17) | N/A |
| 52032 caCAGGCTCC AGGAAGGgtt tggcctct (SEQ ID NO: 12) | RSDHLTQ (SEQ ID NO: 13) | QSGHLAR (SEQ ID NO: 14) | QSGTRNH (SEQ ID NO: 24) | QSSDLSR (SEQ ID NO: 16) | RRDNLHS (SEQ ID NO: 17) | N/A |
| 51541 caCAGGCTCC AGGAAGGgtt tggcctct (SEQ ID NO: 12) | RSDHLTQ (SEQ ID NO: 13) | QSGHLAR (SEQ ID NO: 14) | QKGTLGE (SEQ ID NO: 15) | RHRDLSR (SEQ ID NO: 18) | RRDNLHS (SEQ ID NO: 17) | N/A |
| 51519 caCAGGCTCC AGGAAGGgtt tggcctct (SEQ ID NO: 12) | RSDHLTQ (SEQ ID NO: 13) | QSGHLAR (SEQ ID NO: 14) | QSGTRNH (SEQ ID NO: 24) | QSSDLSR (SEQ ID NO: 16) | RRDNLHS (SEQ ID NO: 17) | N/A |

TABLE 1-continued

ZFN pairs specific for +58 BCL11A enhancer region

SBS # (target site, 5'-3')

| SBS # (target site, 5'-3') | Design | | | | | |
|---|---|---|---|---|---|---|
| | F1 | F2 | F3 | F4 | F5 | F6 |
| 51534 caCAGGCTCC AGGAAGGgtt tggcctct (SEQ ID NO: 12) | RSDHLTQ (SEQ ID NO: 13) | QSGHLAR (SEQ ID NO: 14) | QKGTLGE (SEQ ID NO: 15) | RGRDLSR (SEQ ID NO: 21) | RRDNLHS (SEQ ID NO: 17) | N/A |
| 51535 caCAGGCTCC AGGAAGGgtt tggcctct (SEQ ID NO: 12) | RSDHLTQ (SEQ ID NO: 13) | QSGHLAR (SEQ ID NO: 14) | QKGTLGE (SEQ ID NO: 15) | RSRDLTR (SEQ ID NO: 29) | RRDNLHS (SEQ ID NO: 17) | N/A |
| 51556 caCAGGCTCC AGGAAGGgtt tggcctct (SEQ ID NO: 12) | RSDHLTQ (SEQ ID NO: 13) | QSGHLAR (SEQ ID NO: 14) | QKGTLGE (SEQ ID NO: 15) | FRQTRAR (SEQ ID NO: 30) | RRDNLHS (SEQ ID NO: 17) | N/A |

*51446 and 51463 differ in linker sequences

All ZFNs were tested for functionality (cleavage activity) and found to be active.

Example 2: Activity of ZFN in Human K562 Cells

Briefly, human K562 cells were cultured in RPMI supplemented with 10% FBS and 200,000 cells were transfected with a suboptimal concentration of 25 ng of each of the plasmid DNA encoding the left and right ZFN partners by Amaxa Nucleofector® following the manufacturer's instructions (Table 2a). In addition, the experiments were performed with 25 ng of the left ZFN and 5 ng of the right ZFN (Table 2b). The Cel-I assay (Surveyor™, Transgenomics) as described in Perez et al. (2008) *Nat. Biotechnol.* 26: 808-816 and Guschin et al. (2010) *Methods Mol Biol.* 649:247-56), was used to detect ZFN-induced modifications of the target gene two or three days after transfection. In this assay, PCR-amplification of the target site was followed by quantification of insertions and/or deletions ("indels") by sequencing. Deep sequencing on the Illumina platform ("miSEQ") was used according to the manufacturer's instructions to measure editing efficiency as well as nature of editing-generated alleles. The results are shown below in Table 2, where the numbers indicate the percent NHEJ activity observed:

TABLE 2a

Matrix screen in K562 cells (25 ng each ZFN)

| | 51949 | 51977 | 51979 | 51982 | 51990 | 51993 | 52015 | 52032 | ave. |
|---|---|---|---|---|---|---|---|---|---|
| 51856 | 22.2 | 21.0 | 27.7 | 23.2 | 21.0 | 23.9 | 17.0 | 26.7 | 22.8 |
| 51857 | 28.5 | 24.4 | 29.4 | 28.1 | 26.7 | 23.9 | 19.2 | 32.8 | 26.6 |
| 51862 | 15.9 | 16.3 | 15.5 | 15.3 | 11.7 | 20.8 | 13.9 | 22.4 | 16.5 |
| 51877 | 12.0 | 13.2 | 12.4 | 13.9 | 10.7 | 11.3 | 9.1 | 13.8 | 12.1 |
| 51879 | 14.2 | 15.1 | 14.9 | 13.8 | 12.0 | 14.4 | 10.8 | 16.8 | 14.0 |
| average | 18.6 | 18.0 | 20.0 | 18.8 | 16.4 | 18.9 | 14.0 | 22.5 | |
| 46801:47923 | 9.3 | | | | | | | | |

TABLE 2b

Matrix screen in K562 cells (25 ng left ZFN, 5 ng right ZFN)

| | 51949 | 51977 | 51979 | 51982 | 51990 | 51993 | 52015 | 52032 | ave |
|---|---|---|---|---|---|---|---|---|---|
| 51856 | 10.9 | 12.6 | 16.9 | 13.4 | 11.0 | 12.4 | 8.5 | 15.5 | 12.7 |
| 51857 | 15.7 | 12.8 | 15.2 | 14.1 | 12.5 | 14.4 | 11.8 | 14.5 | 13.9 |
| 51862 | 13.0 | 11.4 | 13.9 | 10.4 | 14.3 | 12.2 | 12.2 | 14.3 | 12.7 |
| 51877 | 8.2 | 7.2 | 8.8 | 6.7 | 8.2 | 7.1 | 7.0 | 6.9 | 7.5 |
| 51879 | 8.5 | 7.9 | 11.5 | 8.3 | 8.4 | 7.1 | 4.9 | 11.2 | 8.5 |
| average | 11.3 | 10.4 | 13.3 | 10.6 | 10.9 | 10.6 | 8.9 | 12.5 | |
| 46801:47923 | 7.3 | | | | | | | | |

The ZFNs were also constructed using four different linkers between the DNA binding domain and the nuclease domain (see United States Patent Publication No. 20150064789). The linker sequences tested are shown below, where the 'HTKIH' portion of the sequence is the carboxy terminus of the DNA binding domain and the 'ELEEK' portion is the amino terminus of the nuclease domain. The underlined portion is the linker sequence between the two domains:

Linker Sequences

L7a:
(SEQ ID NO: 31)
HTKIH LRGSQLVKSKSEAAAR ELEEK

L7c5:
(SEQ ID NO: 32)
HTKIH LRGSISRARPLNPHP ELEEK

L0:
(SEQ ID NO: 33)
HTKIH LRGSISRARPLNPHP ELEEK

L8c4:
(SEQ ID NO: 34)
HTKIH LRGSYAPMPPLALASP ELEEK

In these experiments, the L0 or L8c4 linkers were tested on the right side partner in combination with the L7c5 or L7a linkers on the left side partner. The combinations of the ZFNs were tested for cleavage activity in K562 cells, and the results (percent NHEJ activity) are shown below in Table 3.

TABLE 3

ZFN activity varying domain linkers

|  | SBS | L7c5 51856 | L7c5 51857 | L7c5 51862 | L7a 46801 | L7a 51446 | ave |
|---|---|---|---|---|---|---|---|
| L0 | 51949 | 6.4 | 9.2 | 7.3 | 4.8 | 10.6 | 7.66 |
| L0 | 51977 | 8.8 | 8.9 | 5.6 | 5.0 | 8.7 | 7.41 |
| L0 | 51979 | 11.4 | 10.5 | 10.8 | 4.5 | 11.3 | 9.70 |
| L0 | 51982 | 8.3 | 9.7 | 9.3 | 4.9 | 10.5 | 8.56 |
| L0 | 51990 | 10.3 | 11.0 | 7.5 | 5.3 | 10.2 | 8.86 |
| L0 | 51993 | 10.7 | 13.5 | 7.3 | 5.1 | 10.9 | 9.52 |
| L0 | 52015 | 8.5 | 8.6 | 7.2 | 5.7 | 6.7 | 7.34 |
| L0 | 52032 | 11.5 | 11.3 | 7.0 | 5.0 | 14.8 | 9.91 |
| L0 | 47923 | 7.6 | 7.6 | 5.0 | 4.0 | 11.5 | 7.14 |
| L8c4 | 52075 | 10.9 | 10.9 | 7.2 | 5.6 | 11.7 | 9.27 |
| L8c4 | 52103 | 9.9 | 8.9 | 8.5 | 3.8 | 10.9 | 8.37 |
| L8c4 | 52105 | 16.7 | 13.0 | 16.3 | 6.3 | 15.2 | 13.49 |
| L8c4 | 52108 | 9.7 | 7.5 | 6.5 | 4.2 | 12.0 | 7.99 |
| L8c4 | 52116 | 12.0 | 15.7 | 9.8 | 4.0 | 13.4 | 10.99 |
| L8c4 | 52119 | 13.1 | 9.8 | 8.3 | 4.5 | 10.3 | 9.19 |
| L8c4 | 52141 | 15.2 | 7.2 | 6.9 | 3.4 | 13.2 | 9.17 |

TABLE 3-continued

ZFN activity varying domain linkers

|  | SBS | L7c5 51856 | L7c5 51857 | L7c5 51862 | L7a 46801 | L7a 51446 | ave |
|---|---|---|---|---|---|---|---|
| L8c4 | 52158 | 9.3 | 10.3 | 7.4 | 3.6 | 12.5 | 8.64 |
| L8c4 | 51536 | 13.3 | 12.1 | 11.3 | 8.0 | 15.4 | 12.04 |
|  | ave-> | 10.76 | 10.32 | 8.28 | 4.88 | 11.65 |  |

Example 3: Activity of the ZFNs in CD34+ Cells

ZFNs as described herein were also tested in human CD34+ cells. For the CD34+ transduction, a BTX ECM830 device with a 2 mm gap cuvette was used. Human CD34+ cells were grown in x-vivo10 media (Lonza) with 1×CC110 (Stem cell Technology) in non-tissue culture treated plates. The cells were counted and collected by centrifugation at 1200 rpm for 10 minutes at room temperature. The cells were washed 1-2× with room temperature PBS. 200,000 cells were used for each transfection, and they were resuspended in 100 μL BTexpress solution. For the CD34+ experiments, RNAs encoding the ZFNs was used rather than DNA. RNA was generated using a mMessageMachine T7 Ultra Kit (Ambion). 500 ng of RNA encoding each ZFN was added per transfection and the mixture was transferred to the cuvette. Immediately following transfer, the mixture was electroporated at 250V for 5 msec. Pre-warmed media was added to the cuvette and the media plus cells were transferred to a 48 well non-tissue culture treated plates and then incubated at 37° C.

After two or three days, the cells were then were subject to genome analysis using an Illumina MiSeq. To quantitate the percent of edited alleles, the genomic region of interest was PCR amplified using primers which add the standard Illumina sequencing adapter sequences. A second group of 13 rounds of PCR was performed to add barcode and bridge adapter sequences to both ends. Sequencing was performed on an Illumina MiSeq according to manufacturer's protocols for amplicon sequencing. The MiSeq generates paired-end reads, which are merged and adapter-trimmed using a standard alignment software. Reads were then demultiplexed by sample via barcode sequence pairs using custom scripts. Amplicon sequences were then globally aligned to a reference sequence via an implementation of the Needleman-Wunsch algorithm (Needlemanand Wunsch (1970). *Jour Mol Bio* 48 (3): 443-53). Gaps or insertions in the alignment were counted as % NHEJ events, and compared to an untreated control sample sequence to determine sequence-specific background rates. The results are shown below in Table 4.

TABLE 4

ZFN activity in CD34+ cells

|  | 51949 | 51977 | 51979 | 51982 | 51990 | 51993 | 52015 | 52032 | 51536 | ave |
|---|---|---|---|---|---|---|---|---|---|---|
| 51856 | 38.4 | 11.9 | 26.9 | 23.9 | 37.3 | 37.0 | 26.4 | 32.1 | nd | 29.2 |
| 51857 | 52.1 | 17.2 | 39.8 | 30.9 | 51.0 | 43.9 | 35.2 | 53.9 | 40.0 | 40.4 |
| 51862 | 18.4 | 5.2 | 13.0 | 12.4 | 26.6 | 20.7 | 13.7 | 16.2 | 17.7 | 16.0 |
| 51877 | 19.6 | 6.0 | 8.9 | 9.6 | 24.0 | 18.3 | 11.6 | 19.4 | 13.7 | 14.6 |
| 51879 | 36.4 | 10.6 | 21.8 | 19.5 | 39.2 | 30.7 | 21.8 | 34.4 | 22.7 | 26.4 |
| 51446 | 60.1 | 22.6 | 41.2 | 43.6 | 57.8 | 50.4 | 39.7 | 47.6 | nd | 45.4 |
| ave | 37.5 | 12.3 | 25.3 | 23.3 | 39.3 | 33.5 | 24.7 | 33.9 | 23.5 |  |

When an increased amount of input mRNA was used for a selected set of representative pairs (1 µg each ZFN), additional amounts of cutting was observed, as shown in Table 5.

Table 5A and 5B: Increasing ZFN Concentration Leads to Increased Activity

TABLE 5A

| 0.5 ug:0.5 ug | |
|---|---|
| 46801:47923 | 1.6 |
| 51556:51484 | 17.6 |
| 1 ug:1 ug | |
| 46801:47923 | 1.5 |
| 51536:51446 | 49.0 |
| 52032:51446 | 65.7 |
| 52032:51857 | 60.8 |
| 51979:51446 | 60.0 |
| 51979:51857 | 47.5 |
| 51536:51857 | 55.7 |
| GFP | no seq |

TABLE 5B

|  | 51536 | 51541 | 51556 | 51519 | 51534 | 51535 |
|---|---|---|---|---|---|---|
| 51446 | 83.72 | 87.79 | 74.11 | 81.52 | 84.21 | 82.22 |
| 51484 | 75.21 | 84.34 | 64.20 | 67.88 | 79.50 | 74.22 |
| 51463 | 82.71 | 85.24 | 74.00 | 78.81 | 85.53 | nd |
| 51477 | 72.02 | 85.11 | 63.74 | 70.42 | 80.96 | 78.30 |
| 51478 | 72.33 | 82.38 | 58.17 | 66.22 | 75.20 | 70.90 |
| 51487 | 66.27 | 83.26 | 64.11 | 61.97 | 68.99 | 70.42 |

The above transfections were mostly performed under conditions non-saturating mRNA inputs to allow us to best compare the activity of various ZFN combinations. To test the maximum amount of modification obtainable at or near saturating inputs of mRNAs we transfected increasing amounts of 2a constructs or combining two ZFNs in one mRNA into CD34+ cells using BTX electroporation, and the results are shown below in Table 6.

TABLE 6

Modification of the Bcl11a Enhancer with Increasing mRNA input

| 2A: | 2000 ng | 4000 ng | 8000 ng |
|---|---|---|---|
| 51463_2a_51949 | 59.60 | 79.83 | 82.69 |
| 51463_2a_51990 | 67.98 | 80.17 | 77.30 |
| 51463_2a_52032 | 58.58 | 80.36 | 83.26 |
| 51857_2a_51949 | 61.22 | 73.89 | 78.26 |
| 51857_2a_51990 | 60.63 | 70.55 | 74.40 |
| 51857_2a_52032 | 55.84 | 71.17 | 74.29 |
| euf_51446_2a_51536 | 56.36 | 66.69 | 74.85 |
| euf_46801_2a_47923 | 51.15 | 72.20 | 75.97 |

The data in Table 6 show very high modification of the ZFN target region with increasing mRNA input for all combinations tested.

Similar to the experiments done in Experiment 2 analyzing activity with ZFNs comprising varied linkers, the effect of linkers on activity was also tested in CD34+ cells. As above, varying amounts of mRNA (either 500, 1000 or 2000 ng of each) was used to deliver the ZFNs in these experiments. Table 7 shows the effect of linker identity on the activity of the ZFN pairs.

TABLE 7

Effect of linker identity on ZFN activity in CD34+ cells

| | 500 ng | 51463 | 51857 | 1000 ng | 51463 | 51857 | 2000 ng | 51463 | 51857 |
|---|---|---|---|---|---|---|---|---|---|
| L0 | 51949 | 29.9 | 31.0 | 51949 | 48.8 | 46.7 | 51949 | 44.5 | 43.5 |
| | 51979 | 26.3 | 23.8 | 51979 | 39.2 | 40.0 | 51979 | 36.3 | 35.1 |
| | 51990 | 28.6 | 28.1 | 51990 | 39.8 | 41.8 | 51990 | 36.1 | 36.3 |
| | 52032 | 24.7 | 25.5 | 52032 | 39.6 | 39.7 | 52032 | 37.2 | 33.6 |
| L8c4 | 51536 | 23.0 | 19.1 | 51536 | 36.0 | 31.0 | 51536 | 35.7 | 30.6 |
| | 52075 | 22.1 | 21.2 | 52075 | 34.7 | 32.0 | 52075 | 35.2 | 27.5 |
| | 52105 | 21.9 | 19.1 | 52105 | 37.2 | 32.8 | 52105 | 36.2 | 31.6 |
| | 52116 | 14.7 | 13.9 | 52116 | 27.6 | 28.8 | 52116 | 28.4 | 28.9 |
| | 52158 | 22.2 | 21.1 | 52158 | 36.3 | 34.9 | 52158 | 41.7 | 38.2 |
| | 500 ng | 51446 | | 1000 ng | 51446 | | 2000 ng | 51446 | |
| | 51536 | 19.8 | | 51536 | 35.5 | | 51536 | 28.7 | |

Example 4: Differentiation of Edited CD34+ Cells and Hemoglobin Expression

To test the effect on relative gamma globin expression, the mRNAs encoding a representative sample of the ZFN pairs were introduced into CD34+ cells (obtained from healthy donor volunteers) by BTX nucleofection according to manufacturer's instructions. The cells were then differentiated into erythrocytes. Briefly, CD34$^+$ cells were purified using Ficoll-Paque (GE Healthcare) and CD34' microbeads (Miltenyi Biotec) according to the manufacturers' instructions. CD34$^+$ cells were cultured in Iscove's MDM with BIT 95000 (StemCell Technologies) in the presence of growth factors. Cells were differentiated toward the erythroid lineage using a 3 step liquid culture model. During the first 6 days (first phase), CD34$^+$ cells were expanded with SCF (100 ng/ml), Flt3-L (100 ng/ml), and IL-3 (20 ng/ml). Expanded cells were then committed and differentiated toward the erythroid lineage (second phase) with Epo (2 U/ml) and SCF (50 ng/ml). See, Giarratana et al. (2011) *Blood* 118(19):5071-9.

To analyze relative gamma globin expression, the ratios of mRNAs encoding gamma globin, alpha globin and beta globin following ZFN treatment were determined at 14 days after the start of differentiation by RT-PCR analysis. The analysis was done by standard Taqman® analysis, following the protocol and using gene specific assays supplied by the manufacturer (Applied Biosystems). The relative levels of gamma globin (HBG) was normalized by the level of alpha (HBA) or beta globin (HBB) expression where the ratio was compared to the gamma/alpha or gamma/beta ratio in control cells.

The data are presented below in Table 8, and demonstrate that in comparison with cells that were treated with the GFP encoding plasmid, there was an increase in gamma globin expression in ZFN-treated cells.

TABLE 8

Change in gamma globin expression relative to alpha or beta globin in edited CD34+ cells

| ZFN pair | HBG/HBA | HBG/HBB |
|---|---|---|
| 46801/47293 | 2.7 | 4.4 |
| 51446/51536 | 5.0 | 8.1 |
| 51463/51536 | 8.0 | 10.5 |
| 51484/51536 | 3.8 | 6.4 |
| GFP | 1.6 | 2.8 |

In vitro erythroid differentiation of the CD34+ cells transfected at or near saturating mRNA concentrations followed by RT-PCR analysis of globin expression as described above shows very efficient gamma-globin activation by all selected ZFN pairs targeting the Bcl11a enhancer when compared to the GFP mRNA transfected control sample (FIG. 1). The data is presented below in Table 9.

TABLE 9

Increased ratio of human gamma globin expression

| | HBG/HBB | | |
|---|---|---|---|
| mRNA used | 2 µg | 4 µg | 8 µg |
| 51463-2a-51949 | 10.33 | 17.56 | 21.84 |
| 51463-2a-51990 | 12.75 | 16.05 | 16.96 |
| 51463-2a-52032 | 9.94 | 17.91 | 18.97 |
| 51857-2a-51949 | 10.12 | 14.16 | 12.21 |
| 51857-2a-51990 | 10.36 | 12.37 | 16.47 |
| 51857-2a-52032 | 8.57 | 15.18 | 19.01 |
| 51446-2a-51536 | 9.45 | 10.43 | 14.76 |
| 46801-2a-47923 | 8.86 | 12.15 | 13.10 |
| GFP | 1.65 | | |

Example 5: Activity of ZFN in CD34+ Cells Using a BTX Electroporation Device, Separate mRNAs and Single mRNAs The activity of two pairs of ZFN were tested in mobilized human CD34+ cells isolated from human peripheral blood and in CD34+ cells isolated from bone marrow. Briefly, the CD34+ cells were isolated from healthy donors as follows. Leukapheresis collections were platelet depleted by low speed centrifugation and supernatant removal. Following platelet depletion, the cells were labelled with anti-CD34 magnetic micro-beads (Miltenyi Biotec, Germany) and positively selected using the Miltenyi CliniMACS Plus Cell Separator System. Following selection, the positive fraction (enriched CD34+ HSPC) were washed and resuspended in culture medium (i.e., X-VIVO 10 medium supplemented with 2 mM L-glutamine, 100 ng/mL each of FMS-like tyrosine kinase 3-ligand (Flt-3L), stem cell factor (SCF), and thrombopoietin (TPO)) at 1×106 cells/mL, and transferred into VueLife culture bags (Saint-Gobain, Gaithersburg, Md.) and incubated at 37° C./5% CO2. For purification of CD34+ cells from bone marrow, collections were depleted of red blood cells (RBC) by hydroxyethyl starch sedimentation. Following RBC depletion, the cells were labelled with anti-CD34 magnetic micro-beads (Miltenyi Biotec, Germany) and positively selected using the Miltenyi CliniMACS Prodigy. Following selection, the positive fraction (enriched CD34+ HSPC) were washed and resuspended in culture medium (i.e., X-VIVO 10 medium supplemented with 2 mM L-glutamine, 100 ng/mL each of FMS-like tyrosine kinase 3-ligand (Flt-3L), stem cell factor (SCF), and thrombopoietin (TPO)) at 1×106 cells/mL, and transferred into VueLife culture bags (Saint-Gobain, Gaithersburg, Md.) and incubated at 37° C./5% CO2.

Figure 2A:
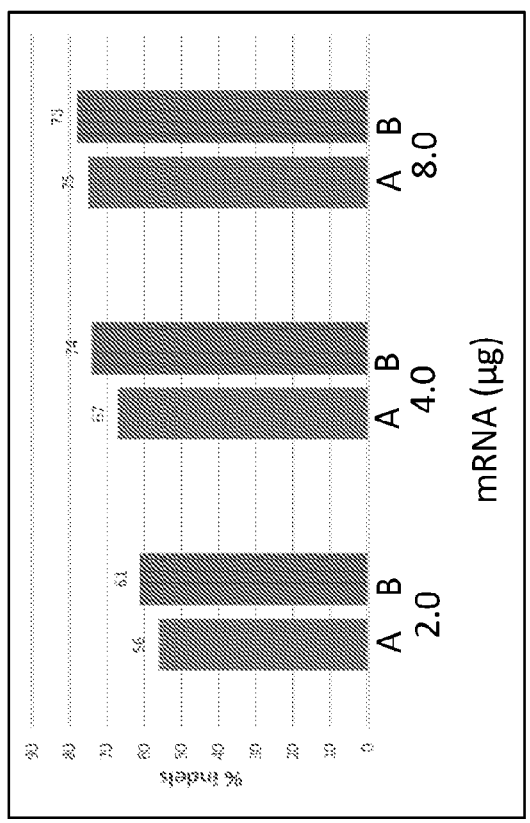
FIGS. 2A and 2B are graphs depicting the activity of two pairs of BCL11a specific ZFNs in CD34+ cells isolated from peripheral blood (PB). Cells were transfected using a BTX electroporation device. The % indels detected (measurement of detectable NHEJ activity) for each condition are shown below the graphs for FIG. 2A (mRNA input range from 0.5 to 4 µg) and FIG. 2B (mRNA input range from 2.0 to 8.0 µg).
Figure 2B:
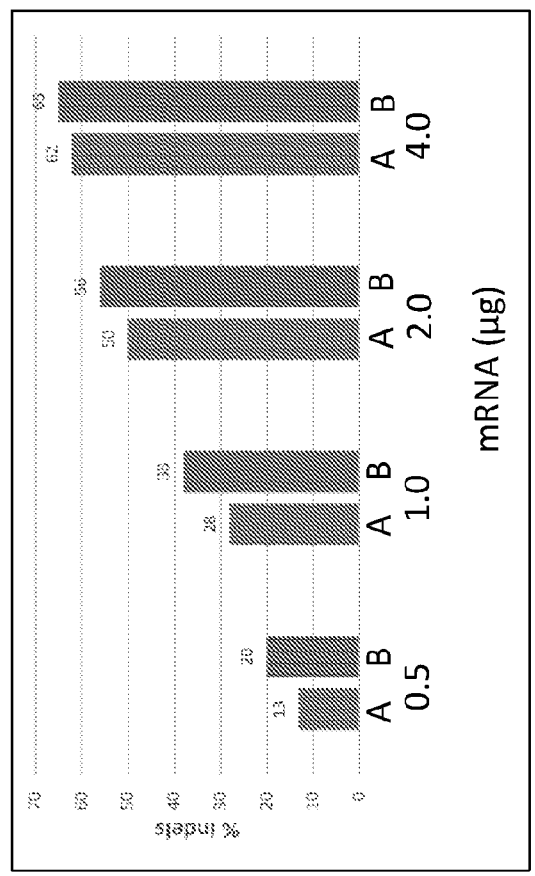

The pairs used were 51446/51536 (pair A) and SBS51857/51949 (pair B). The ZFNs were tested as mRNA introduced into the cells. For transfection, a BTX device was used. Briefly, 200,000 cells per sample were suspended in BTXpress Electroporation solution (BTX) and mixed with the RNA. The mixture was then pulsed for 4 msec at 250 volts and subjected to cold shock conditions (30° C. overnight) prior to letting the cells recover at 37° C. Analysis of ZFN activity was carried out two or three days post-transfection. The ZFNs were tested as single mRNA species, where a 2a self-cleaving peptide sequence was used between the two ZFN coding sequences, and the data is presented in FIG. 2. In addition, the same conditions were used to test 1 pair of ZFN where the provision of the mRNAs was as two separate species, where each mRNA encoded a single ZFN. Table 10a and Table 10b below shows the activity results (% NHEJ or indels) for the single mRNA approach versus two mRNAs (data depicted is from several experiments).

TABLE 10a

Comparison of single versus double mRNA species (% indels)

| mRNA used | 2.0 µg | 4.0 µg |
|---|---|---|
| 51857__2a__51949, exp. #1 | 56.0 | 64.7 |
| 51857__2a__51949, exp. #2 | 61.2 | 73.9 |
| 51857 + 51949 | 83.1 | 80.5 |

TABLE 10b

Comparison of single versus double mRNA species (% indels)

| mRNA used | 0.5 µg | 2.0 µg | 4.0 µg |
|---|---|---|---|
| 51857__2a__51949, exp. #3 | 32.0 | 51.5 | 58.7 |
| 51857 + 51949, exp #3 | 40.0 | 58.4 | 63.1 |

Figure 3:
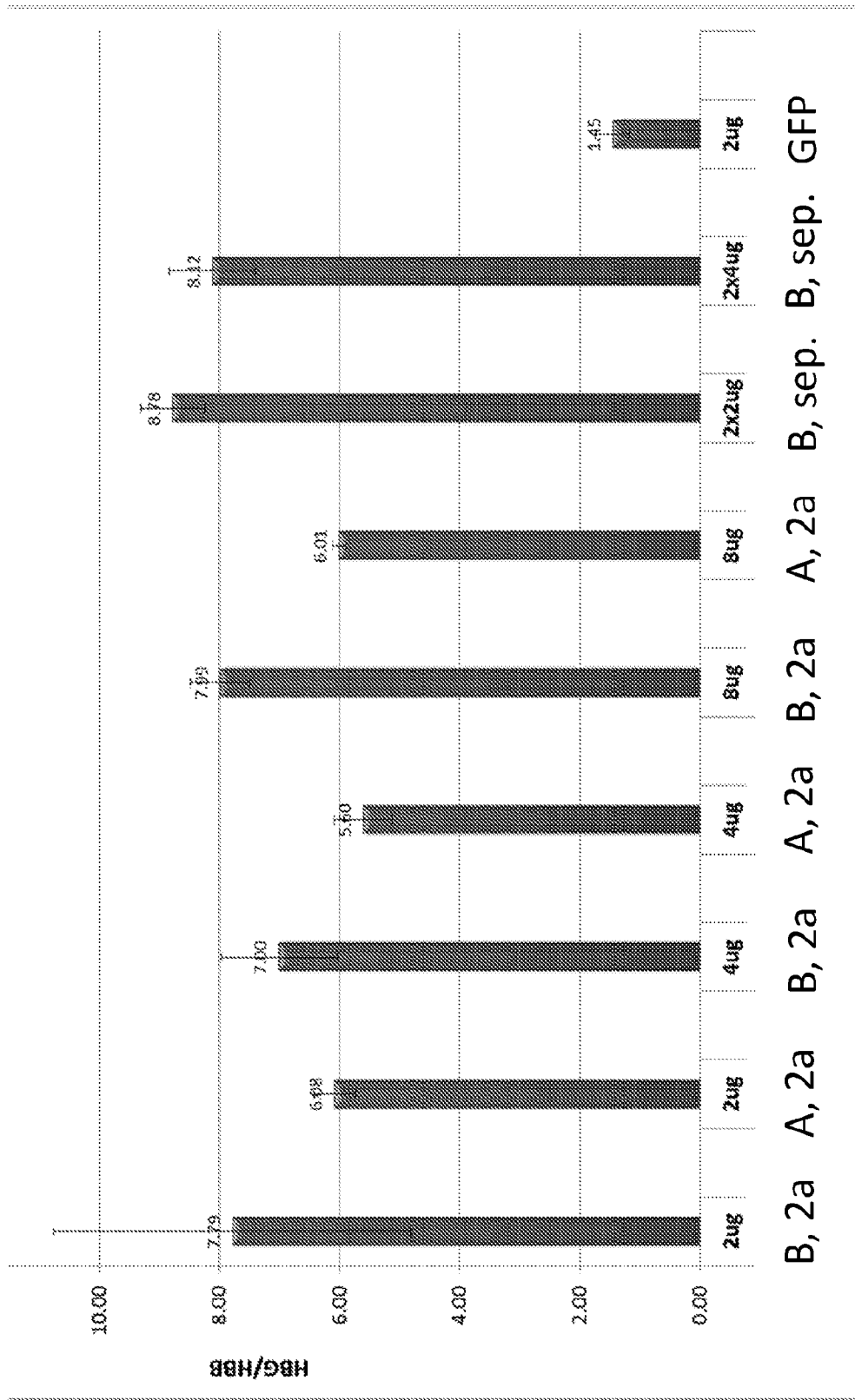
FIG. 3 is a graph depicting the expression of human gamma globin (HBG) as a relative ratio of HBG to human beta globin (HBB) following erythroid differentiation of the edited PB CD34+ cells shown in FIG. 2B. Single mRNA species, where the ZFNs are encoded on the same mRNA molecule but separated by a 2a self-cleaving peptide sequence (identified as "2a"), are compared to the use of two mRNAs where each mRNA encodes one of the ZFN pair (identified as "sep" for separate).

We also tested expression of human gamma globin and human beta globin using TaqMan® according to standard protocols. The results were then normalized as a ration of HBG (gamma) over HBB (beta), and are depicted in FIG. 3, again comparing two pairs of ZFN: 51446/51536 (pair A) and SBS51857/51949 (pair B). In addition, expression of HBG and HBB were also measured comparing the provision of the ZFN pair as a single mRNA, where the sequences encoding each ZFN in the pair are separated by a 2a self-cleaving peptide sequence, with conditions where the mRNA encoding each ZFN was supplied separately. The data demonstrated that under these conditions, the B pair, SB S51857/51949, was more active in cleaving the BCL11a target and in causing an increase in HBG expression.

Figure 4A:
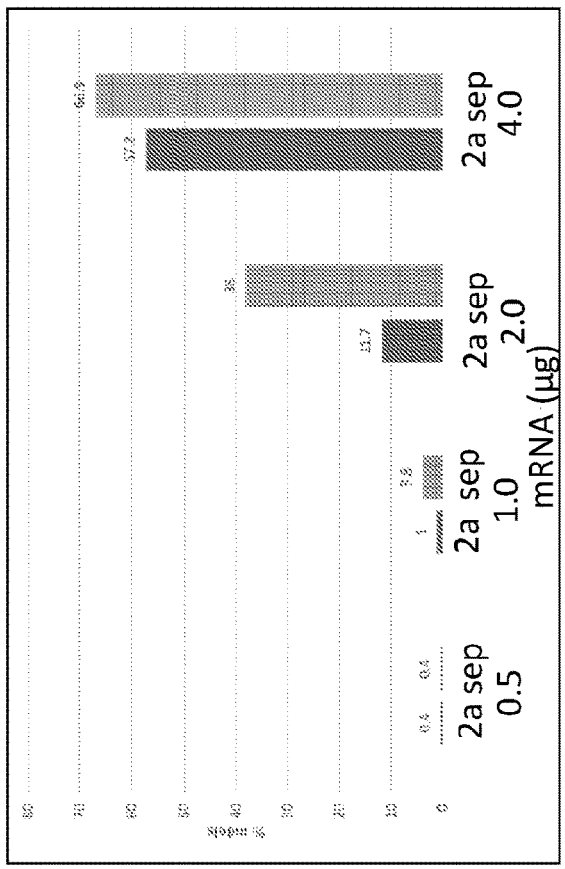
FIG. 4A and FIG. 4B are graphs depicting the activity of two pairs of BCL11a specific ZFNs in CD34+ cells isolated from bone marrow (BM). Cells were transfected using a BTX electroporation device. The % indels detected (measurement of detectable NHEJ activity) for each condition are shown below the graphs for FIG. 4A (mRNA input range from 2.0 to 8.0 µg).
Figure 4B:
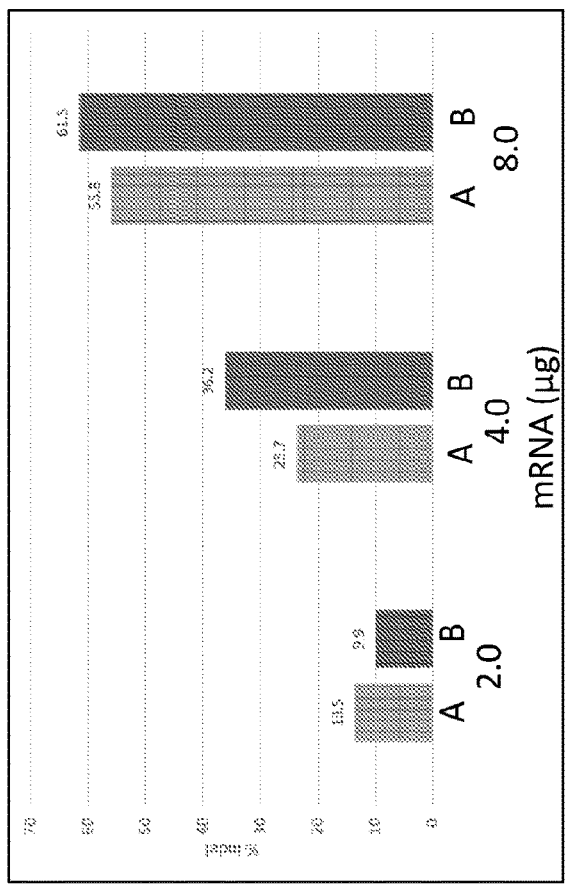

The ZFN pairs were tested in bone-marrow derived CD34+ cells and both pairs were again found to be active (see FIG. 4a). Activity for the SBS51857/51949 pair was also tested where the ZFNs were supplied on a single mRNA with a 2a or as two separate mRNAs as described above (FIG. 4b). The SBS51857/51949 pair demonstrated higher activity than the 51446/51536 pair.

Example 7: Specificity Analysis

Unbiased Capture Analysis:

The capture assay is based on the observation that co-introduction of a nuclease and a duplex DNA donor into a target cell results in the "capture" of donor into a fraction of the resultant genomic break sites via the NHEJ DNA repair pathway (Orlando et al, (2010) Nucleic Acids Res. 38(15) e152; Gabriel, R. et al. (2011). Nat Biotechnol. 29: 816-23.). Note that this capture event is not homology driven (indeed the duplex DNA donor does not contain any homology to the human genome). Note further that the mRNA encoding the ZFNs cannot be captured into the DNA break, solely the duplex DNA donor can. Once trapped the duplex genome represents a permanent tag of the cleavage event. After isolation of genomic DNA, sites of capture may be identified via primer extension from the donor into flanking genome sequence, followed by adapter ligation, PCR, and sequencing of the resulting donor-genome junctions.

Briefly, the capture analysis studies were conducted in the K562 cell line to maximize donor delivery, ZFN expression, and donor capture into DSB sites; the cells were electroporated with the ZFN-encoding mRNA and the oligonucleotide duplex donor. Separately, BM and PB-derived CD34+ cells were electroporated using the Maxcyte device as described above with the ZFN-encoding mRNA. The duplex donor oligonucleotide used is shown below (SEQ ID NOs: 37 and 38):

```
5' NNNNAGTAGTGTGTGCCCGTCTGTTGTGTGACTCTGGTAACTAGAG
ATCCCTCAGACCCTTTTAGTCNNNNNNAGTGTGGAAAATCTCTAGCAG 3'

3' TCATCACACACGGGCAGACAACACACTGAGACCATTGATCTCTAGG
GAGTCTGGGAAAATCAGNNNNNNTCACACCTTTTAGAGATCGTCNNNN 5'
```

The NNNN at the 5' end of each strand indicates a random, single strand tetramer overhang, while the underlined NNNN indicates random duplex sequence that served as a bar code to differentiate between otherwise identical integration events. Triplicate samples were prepared for each combination of oligo and mRNA. On days 7 and 14 post-transfection genomic DNA was isolated (Qiagen DNeasy Blood and Tissue Kit), and 1 μg (330000 genomes/replicate) was used as input for the amplification protocol. Samples were then processed essentially as described (Paruzynski, A. et al. (2010). Nat. Protocols. 5:1379-1395). Amplicons were purified using a QIAquick PCR Purification Kit (Qiagen), and amplified by PCR to introduce barcodes and adapters for deep sequencing on the Illumina platform. Final products were quantified, pooled and sequenced on a MiSeq Instrument (Illumina) using a v2 300 cycle sequencing kit with paired-end 150 bp reads and 8 bp dual index reads to detect the barcodes on each end of the amplicon. This effort yielded a set of candidate off-target loci that were then genotyped in BM- or PB-derived CD34 cells The results identified for pair A (SBS #51446/51536) are shown in FIG. 10a, while the results for pair B (SBS #51857/51949) are shown in FIG. 10b. The data is further summarized below in Table 11.

TABLE 11

Off target analysis for pair A and pair B, CD34+ from Bone Marrow

| A | 250 ug/ml | 63% | 21 | 9% |
| B | 125 ug/ml | 63% | 9 | 3% |
| B | 250 ug/ml | 74% | 20 | 17% |

Similar studies were performed on CD34+ cells derived from PB, and Table 12 below summarized the results found.

TABLE 12

Off target analysis for pair A and pair B, CD34+ from Peripheral Blood

| ZFNs | Dose | On-Target | # off-targets | Cumulative Activity |
|---|---|---|---|---|
| St 4 | 120 ug/ml | 60% | 11 | 4% |
| St 5 | 120 ug/ml | 56% | 10 | 3% |

Figure 5B:
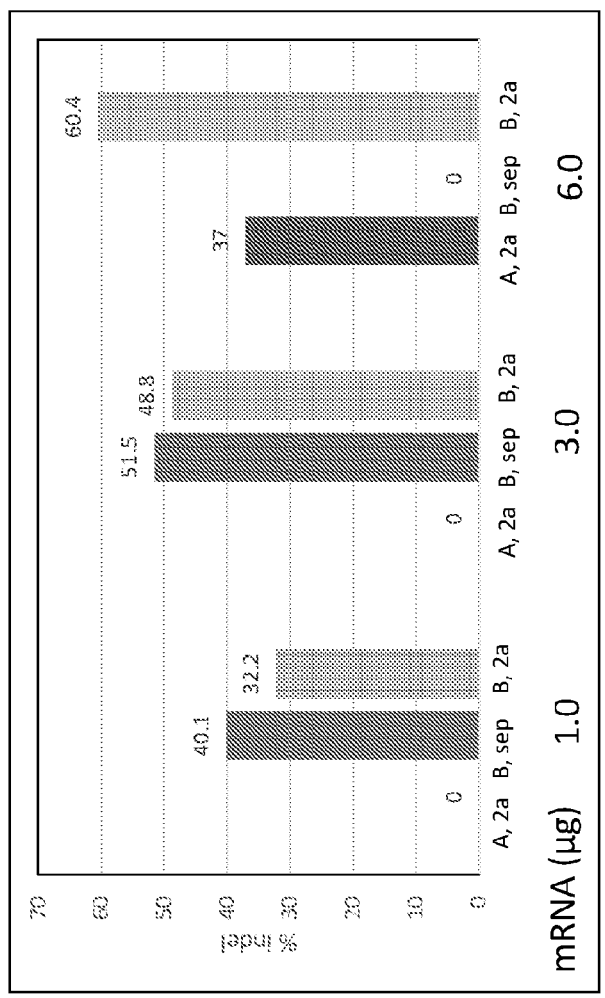

Example 6: Activity of ZFN in CD34+ Cells Using a Maxcyte Electroporation Device, Separate mRNAs and Single mRNAs We next ran larger scale experiments using the ZFN pairs in CD34+ cells using a Maxcyte GT electroporation device. Mobilized CD34+ cells isolated peripheral blood from normal donors as described above (PB) were tested as follows: cells (3 million per sample) were resuspended in RT Maxcyte EP buffer to a final concentration of 30 e6 cells/mL. Cells were mixed with mRNA and electroporated using the program specified by manufacturer. Cells were allowed to recover briefly at 37° C. for twenty minutes, then diluted and subjected to cold shock conditions (30° C. overnight) prior to letting the cells recover at 37° C. Activity was analyzed two to three days later. Experiments were done with both the A pair and the B pair as previously, where each pair was introduced on a single mRNA (FIG. 5A). The ZFN pair B (SBS51857/51949) was also tested as a single mRNA or two separate mRNAs as described above (FIG. 5b). In these experiments, the B pair showed the highest activity.

Figure 6:
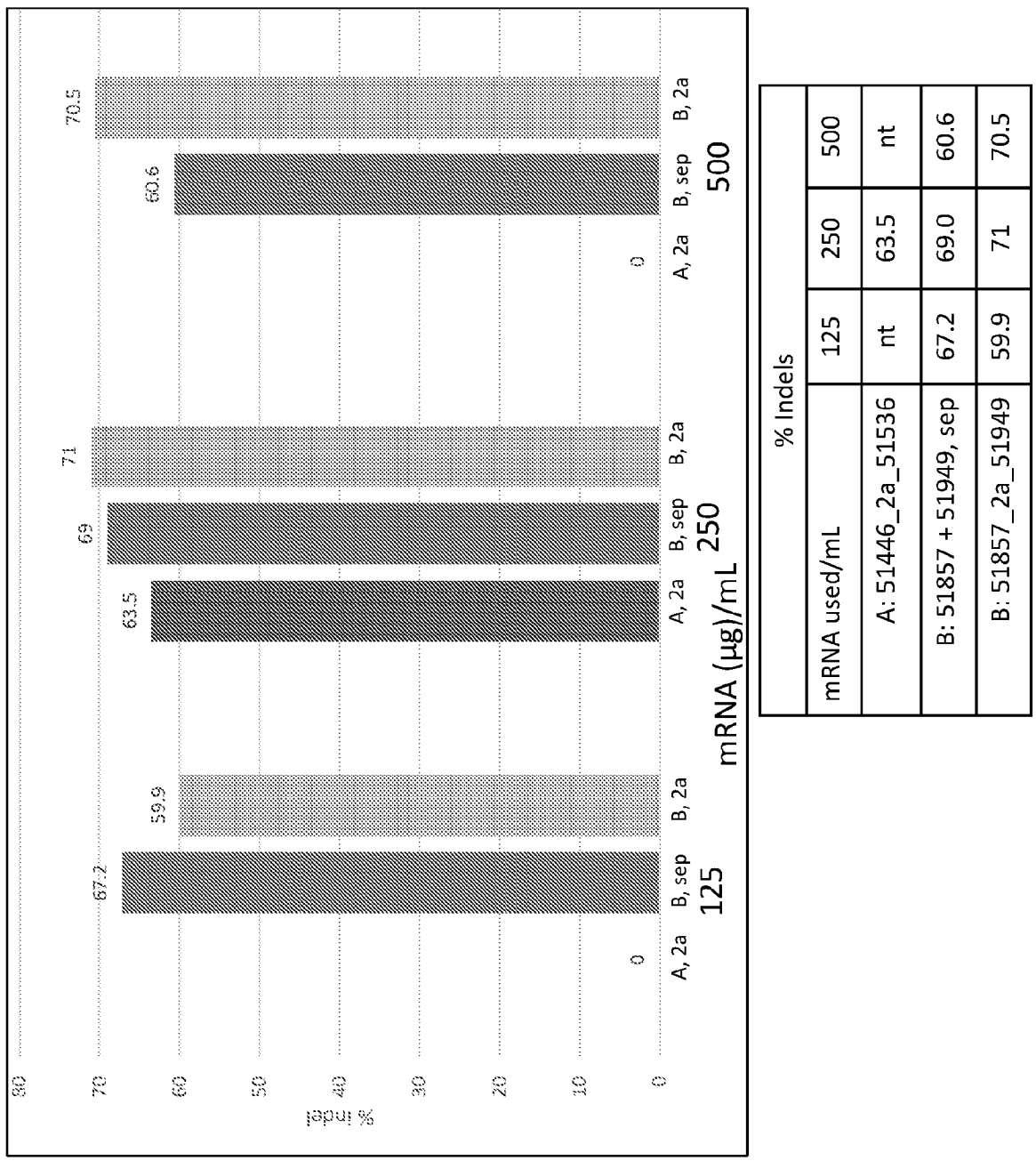
FIG. 6 depicts a graph showing large scale activity of the A pair (SBS51446/51536) and B pair (SBS51857/51949) in bone marrow derived CD34+ cells. mRNAs encoding the ZFN pairs were either supplied as single mRNAs where the sequences encoding each half of the ZFN pair were separated by a 2a self-cleaving sequence, or as separate mRNAs encoding each ZFN. Activity is shown in the % indels detected.
Figure 7:
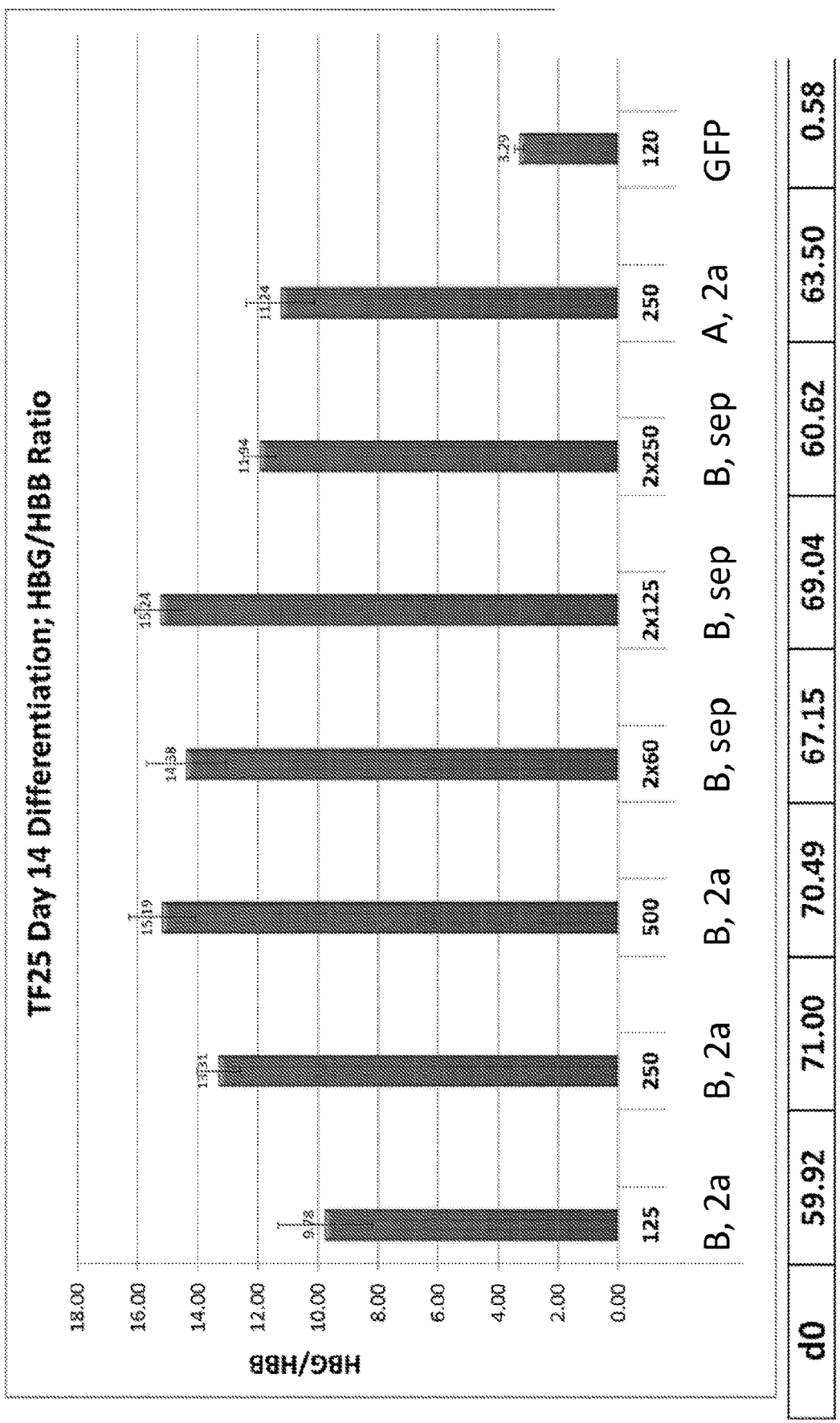
FIG. 7 shows a graph depicting the relative amount of HBG and HBB expression detected after 14 days of differentiation following the large scale gene editing shown in FIG. 6. As before, samples were tested either as single mRNAs encoding both ZFNs, or as separate mRNAs. The amount of indels detected at day 0 of differentiation is shown across the bottom, and demonstrates that indel activity tracks with the amount of HGB expressed.

For bone marrow derived cells, successful editing required more mRNA, but high activity was observed (see FIG. 6). The cells were analyzed for HBG and HBB expression as described above and the HBG/HBB ratio compared to the percent indel activity at day 0 (FIG. 7). There was a good agreement between higher levels of HBG expression and higher indel activity.

Figure 8:
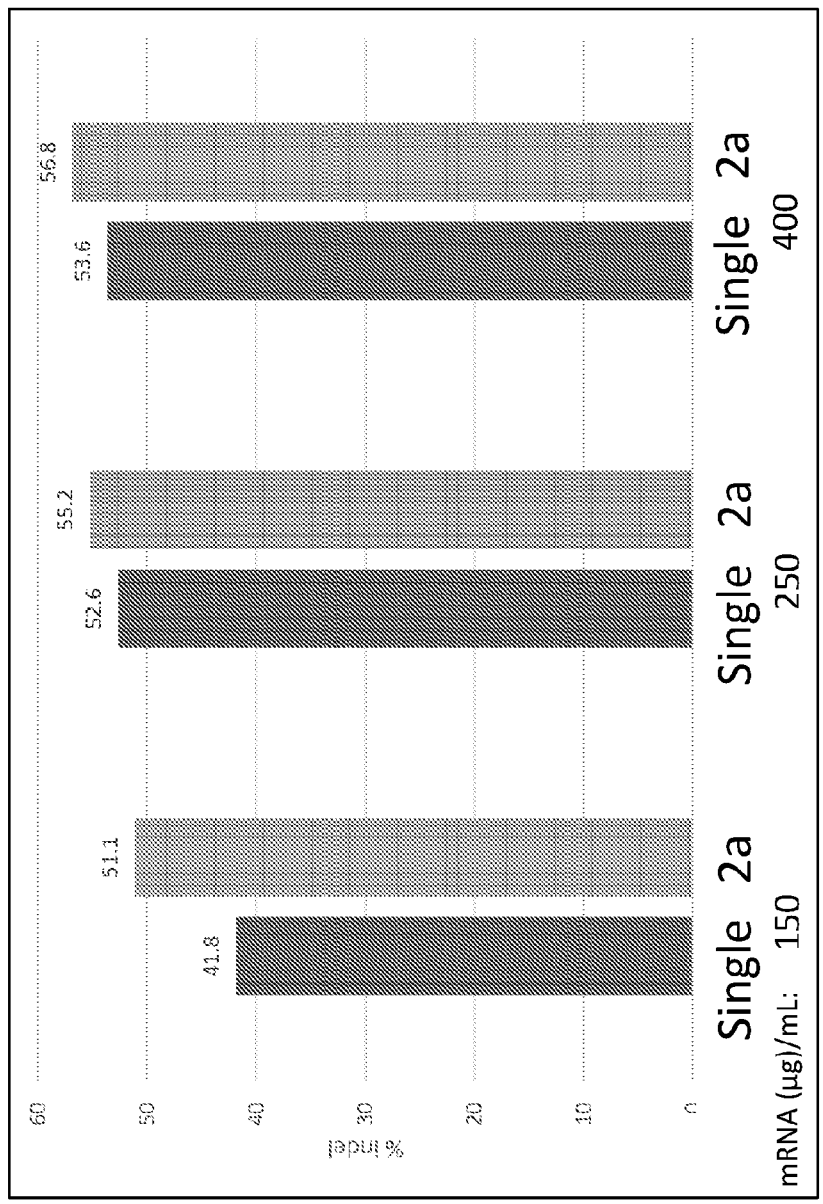
FIG. 8 is a graph depicting the percent of indels detected in large scale editing of CD34+ cells from bone marrow treated with pair B, either as single mRNAs or separate mRNAs as described above.
Figure 9A:
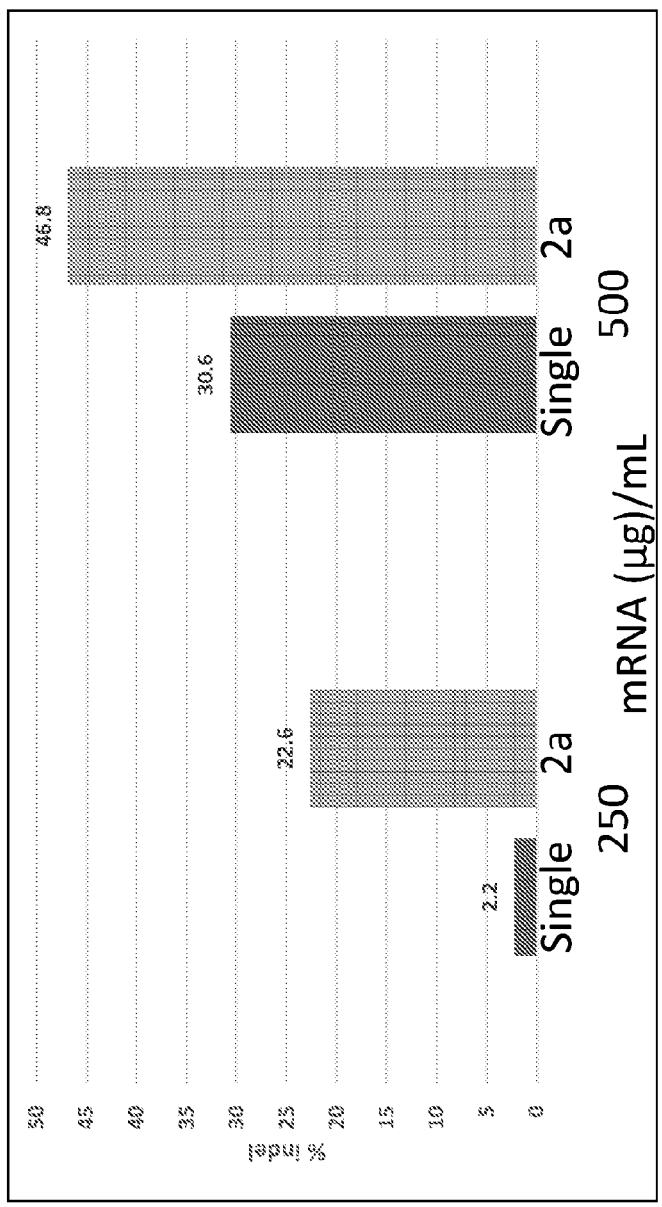
FIGS. 9A and 9B are graphs depicting the percent of indels detected in large scale editing of CD34+ cells from bone marrow treated with pair B, either as single mRNAs or separate mRNAs as described above.
Figure 9B:
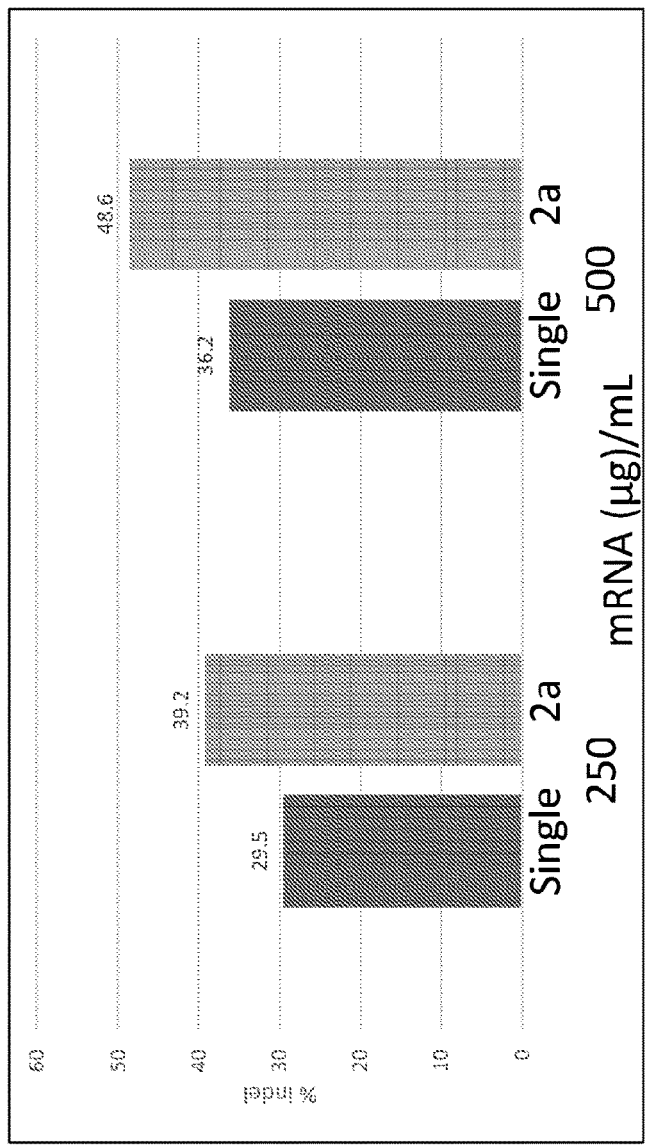

More analyses were done using the Maxcyte protocol (FIGS. 8 and 9) where it was found that although the frequency of indels wasn't always the same in each experiment, the relative activity (e.g., 2a SBS51857/51949 construct higher than the separate mRNAs) was observed in each run.

Example 7: Engraftment of Edited Human CD34+ Cells in Mice

As described above, CD34+ human cells are treated with mRNAs encoding the +58 enhancer specific ZFNs and then engrafted into NSG mice. CD34+ cells are obtained from healthy human volunteers. In some cases, CD34+ mobilization strategies were done, using either G-CSF (Neupogen®) or G-CSF+ Plerixafor (Mozobil®) prior to apheresis. The G-CSF is administered daily for the four days prior to apheresis according to manufacturer's instructions, and if Plerixafor was used, it was administered on the final evening prior to harvest, again according to manufacturer's instructions. The apheresis is performed by standard methods. CD34+ cells were enriched from the mobilized PBMC leukopaks using a Miltenyi CliniMACs system by standard methods and according to manufacturer's instructions.

Capped and poly-adenylated mRNAs encoding the ZFNs are synthesized using Ambion mMessage mMachine® T7 ultra kit as instructed by the manufacturer and then electroporated into the CD34+ cells using either a Maxcyte GT system or a BTX ECM830 electroporator, both according to manufacturer's instructions.

NOD.Cg-Prkdc$^{scid}$ Il2rg$^{tm1Wjl}$/SzJ mice are used to receive the CD34+ transplant. One day (16-24 hours) prior to implantation, the mice are subject to sub lethal irradiation (300 RAD). The ZFN-treated CD34+ cells from above are transplanted into the irradiated mice through a tail vein injection, where 1 million cells in 0.5 mL PBS-0.1% BSA were given per mouse.

For this experiment, CD34+ cells are electroporated with mRNAs encoding the 46801/47923 pair. Genes encoding the ZFNs are cloned together in a single open reading frame separated by a sequence encoding a 2A self-cleaving peptide. GFP was used as a control. Following transplantation into the mice, samples are taken at either 4, 8 and 12 weeks post-transplant to observe the level of human cell specific marking in cells.

The ZFN-edited CD34+ cells engraft and differentiate, and levels of engraftment are similar between the edited cells as compared to the unedited controls.

Example 8: Activity of ZFNs in Patient Derived Cells

The activity of the ZFN were tested in mobilized human CD34+ cells isolated from human peripheral blood and in CD34+ cells isolated from bone marrow. HSPC from five β thalassemia subjects (designated P11, P18, P04, P08 and P19) were mobilized and purified as described (Yannaki et al. (2012) Mol Ther 20(1):230). In both experiments, 200,000 CD34+ cells were electroporated two days after thawing, using a BTX electroporator (Holliston, Mass., Voltage=250 V, pulse length=5 ms) in 100 μL of BTX Express electroporation solution. Transfections used either 4 μg of green fluorescent protein (GFP) encoding mRNA (as a control for electroporation efficiency, and to control for nonspecific effects of electroporation itself, and for nonspecific effects of introducing mRNA into the cells), or 4 g and 8 g of SB 51857-2a-51949 mRNA.

In a small scale transfection using the BTX electroporator these SB 51857/51949 mRNA amounts resulted in equivalent target gene modification and γ-globin activation to the 80-120 ug/ml concentrations used in the larger scale MaxCyte device transfections.

Following electroporation, a transient overnight culture at 30° C. was performed. Cells were cultured for an additional 48 hours at 37° C. whereupon in vitro differentiation was initiated and cell aliquots were harvested for analysis of DNA modification. After transfection, cells were cultured in X Vivo 10 medium (Lonza, Walkersville, Md.) supplemented with the CC 100 cytokine cocktail (Stem Cell Technologies, Vancouver, Canada).

BCL11A gene modification was measured by MiSeq deep sequencing 72 hours after electroporation, at the time when the in vitro differentiation was started (therefore d3 post-transfection was d0 of the differentiation) and at day 14 of the erythroid differentiation. The results are shown in Table 13.

The patient derived CD34+ cell samples we obtained had been frozen twice prior to use, and therefore some of these sample exhibited reduced viability and cell growth upon thawing. Low viability post-thaw has been observed to coincide with higher reduction in viability after transfection and with lower target gene modification, especially at the early time points, when the DNA from non-transfected dead cells is still present. As an SB-ZFN transfection independent indicator of cell viability after transfection, Table 13 shows cell viability for each cell source in the control sample which was transfected with GFP mRNA. The table shows that patient cell samples P18 in experiment 1 had much lower viability (38%) than the other two samples (71% and 80%) in this experiment and did not reach the same modification levels of ~70% alleles modified. Similarly in the second experiment at day 3 patient cell sample P08 showed very poor viability (22%) and very low early modification levels and suboptimal modification levels even after expansion and outgrowth of the healthy cells.

TABLE 13

BCL11A Gene Modification Analysis by MiSeq

| | Cell source | GFP Control Viability d3 (%) | SB-mRENH mRNA (μg) | Target Gene Modification (%) | |
|---|---|---|---|---|---|
| | | | | Day 3 | Day 14 |
| Experiment 1 | WT | 71 | 4 | 70 | 69 |
| | | | 8 | 72 | 69 |
| | P11 | 80 | 4 | 70 | 71 |
| | | | 8 | 73 | 73 |
| | P18 | 38 | 4 | 45 | 53 |
| | | | 8 | 51 | 59 |
| Experiment 2 | WT | 89 | 4 | 71 | 72 |
| | | | 8 | 77 | 77 |
| | P04 | 62 | 4 | 48 | 62 |
| | | | 8 | 53 | 67 |
| | P08 | 22 | 4 | 19 | 62 |
| | | | 8 | 32 | 68 |
| | P19 | 68 | 4 | ND | 69 |
| | | | 8 | ND | 73 |

ND = no data,
WT = wild type

These data show that disruption of the BCL11A enhancer following electroporation of SB ZFN mRNA into G CSF mobilized, purified HSPCs from healthy donors and from thalassemia patients with β thalassemia occurred in most samples within the range expected for clinical samples. As a consequence of the low viability of some of the samples, enhancer disruption in P18 and P08 was lower than in cells from healthy donor volunteers, and consequently the two samples with low viability were omitted from the analyses below. Importantly, samples from subjects that exhibited robust cell viability (e.g. samples P11 and P04) also exhibited gene modification levels equivalent to those seen in the wild type cells.

Figure 11A:
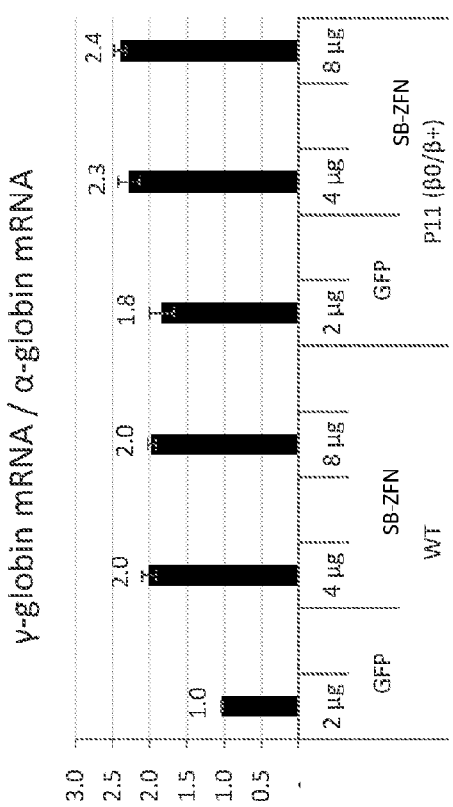
FIGS. 11A and 11B are graphs showing real-time RT qPCR analysis of in vitro differentiation in experiment 1 (FIG. 11A) and experiment 2 (FIG. 11B) using patient and wild type (wt) cells treated with SB ZFN mRNA. The graphs show the relative ratios of gamma globin to alpha globin mRNAs.
Figure 11B:
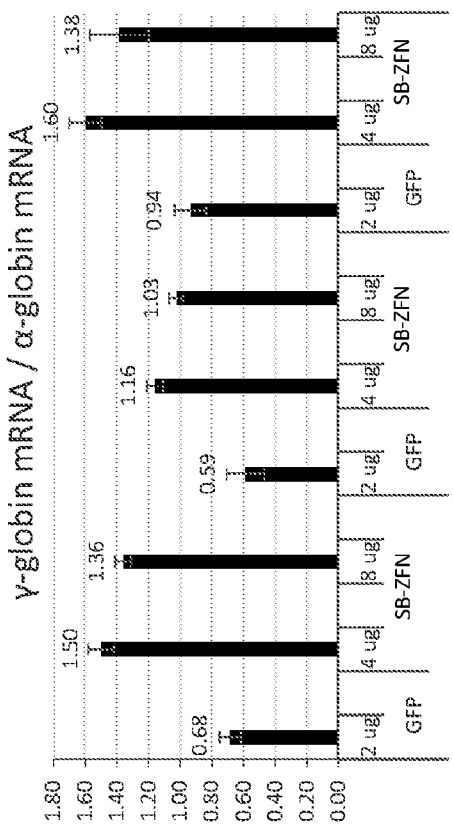
Figure 12A:
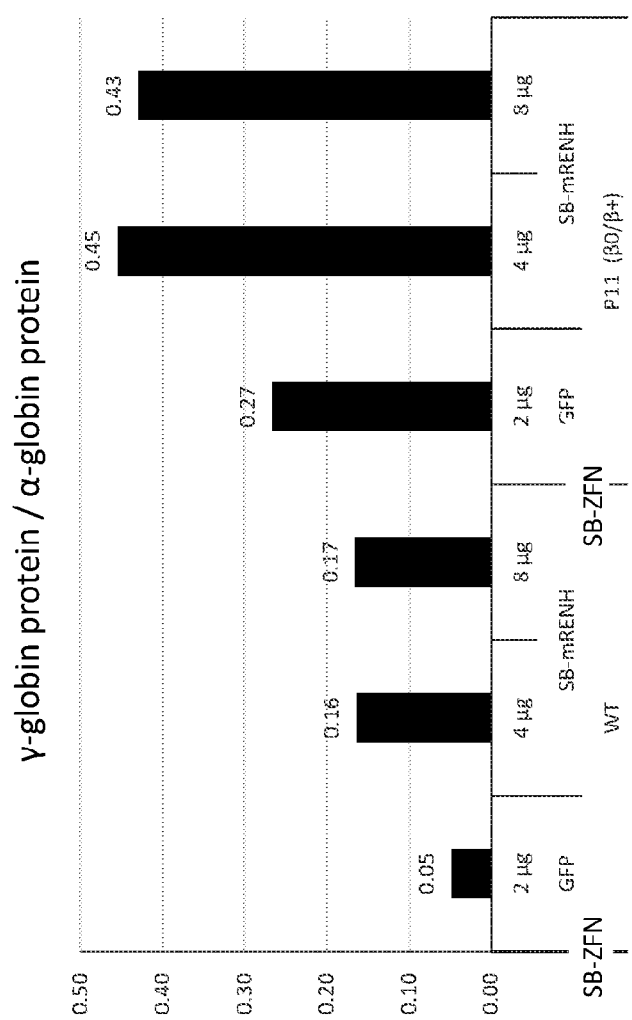
FIGS. 12A and 12B are graphs showing the ratios of gamma globin to alpha globin in experiment 1 (FIG. 12A) and experiment 2 (FIG. 12B). For the gamma globin values, the values of the Agamma and Ggamma peaks and, where applicable, the Agamma T peak were added up.
Figure 12B:
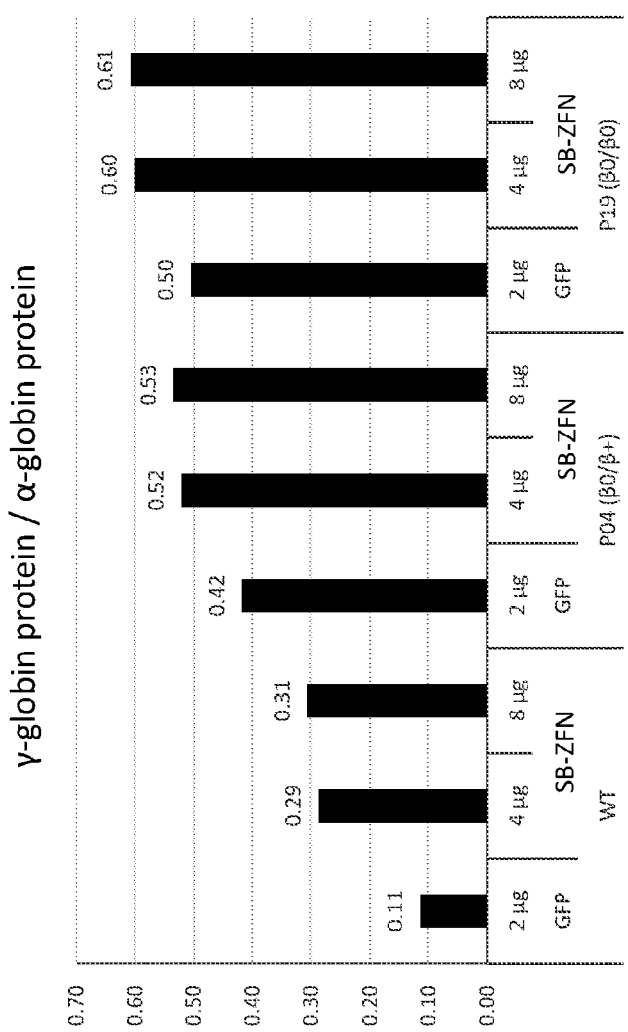

Levels of α and γ globin mRNA isolated from erythroid progeny of CD34+ HSPC from subjects with β thalassemia showed an increase in fetal (γ) globin levels following treatment with SB ZFN mRNA when analyzed by RT qPCR (FIG. 11). Fetal γ globin mRNA levels are shown normalized relative to α globin mRNA since the thalassemia cells expressed low or no β globin mRNA.

Erythroid progeny of CD34+ HSPCs from subjects with β thalassemia treated with SB ZFN mRNA reveal the anticipated increase in the ratio of fetal (γ) globin mRNA to α globin mRNA, reaching gamma-globin to alpha-globin ratios similar to those seen in the wild type donor cells, in particular in the patient samples that showed good viability after thawing and consequently target gene modification levels comparable to those in wild type cells.

Reverse phase HPLC was then used to determine whether modification of the BCL11A erythroid enhancer elevates fetal hemoglobin at the protein level.

The gamma globin (sum of the Agamma and Ggamma peaks)/alpha globin ratios for the two experiments showed a clear elevation of fetal globin protein was observed in red blood cells (RBCs) derived from healthy volunteers and thalassemia patients upon SB ZFN disruption of the BCL11A enhancer, even though the untreated gamma/alpha ratios in the thalassemia cells especially in β0/β0 cells are usually well above those in the wild-type (wt) cells. Analysis of fetal to adult globin ratios in cells from patients with β thalassemia major is complicated by the fact that the tetramerization and precipitation of α globin in unmodified cells eliminates it from the HPLC analyzable pool.

Thus, solely α globin tetramerized with residual β globin (in patients with β+ thalassemia) and γ globin, or solely α globin tetramerized with γ globin (in β0/β0 cells) can be revealed in the assay. Therefore, if γ globin protein levels increase, productively tetramerized α globin protein levels can increase as well and the γ/α globin protein ratio underestimated the increase in γ globin protein levels. Another ratio that was useful to examine in wild type cells was the γ globin/β like protein ratio (the latter being the sum of the two γ globin protein levels plus δ globin plus β globin). However in thalassemia patient cells, particular in the β0/β0 cells, this ratio was usually over 90% even in non ZFN treated cells and even substantial increases in γ globin protein levels after ZFN treatment did not markedly increase this ratio.

Example 9: Analysis of Modified Allele Distribution and Effect on Fetal Globin in ZFN Treated Wild Type CD34+ Cells We also evaluated erythroid cells derived from CD34+ cells treated with SB ZFN, at the single cell level with respect to two endpoints: (1) distribution of alleles of BCL11A erythroid enhancer region rated by the action of the ZFNs between individual cells, and (2) effect of the distribution of individual alleles (wild type and genetically modified) on levels of fetal globin (as gauged by the γ/β globin mRNA ratio). Thus, single CD34+ cells found in SB ZFN HSPC were sorted and differentiated in vitro. The resulting single cell derived colonies of hemoglobinized cells were harvested individually; genomic DNA (gDNA) for each of the colonies was sequenced at the SB ZFN target region in the BCL11A erythroid enhancer to determine whether the locus has been disrupted, and if yes, what precise allelic form of the locus was generated. Further, total RNA was isolated from the same colony, and globin expression levels in these individual clones were analyzed by real time reverse transcription quantitative polymerase chain reaction (RT qPCR).

Methods

For single cell studies, transfected SB ZFN HSPC cells were thawed at 37° C., added to 10 mL X VIVO at room temperature, and spun down at 450× g for 5 minutes at room temperature. Cell pellets were resuspended at 1×106/mL in X VIVO media supplemented with Flt3L, TPO, and SCF (100 ng/mL each), penicillin (100 U/mL), and streptomycin (100 µg/mL). After overnight culture in a 24 well non tissue culture-treated plate at 37° C., 5% CO2 in a humidified incubator, cells were collected, spun down, and resuspended in phosphate buffered saline (PBS) supplemented with 0.5% bovine serum albumin at 2×106/mL. Cells were sorted into Step 1 erythroid culture media (200 µL/well) in 96 well U bottom non-TC treated plates at 2 cells/well using FACS Aria III. Step 1 erythroid culture media consisted of Glutamax containing Iscove's Modified Dulbecco's Medium (IMDM) supplemented with 100 U/mL penicillin, 100 µg/mL streptomycin, 5% human AB+ plasma, 330 µg/mL human holo transferrin, 20 µg/mL human insulin, 2 U/mL heparin, 3 U/mL recombinant human erythropoietin, 100 ng/mL SCF, 5 ng/mL IL 3, and 1 µM/mL hydrocortisone. After 7 days of culture at 37° C., 5% CO2 in Step 1 erythroid culture media, 150 µL of media per well was removed and replaced with 100 µL Step 2 erythroid culture media, which was similar to Step 1 media but without the addition of IL 3 and hydrocortisone. After 4 additional days of culture, 100 µL media per well was removed and replaced with 100 µL Step 3 media, which was similar to Step 2 media but without SCF.

On Day 14 post differentiation, 10 µL of cell suspension per well was harvested for deep sequencing. Furthermore, 100 µL of media per well was removed and replaced with 100 µL of fresh Step 3 media. Remaining cells were cultured for 3 more days when 50 µL of cell suspension per well was collected, stained with an equal volume of NucRed (2 drop/mL in PBS 0.5% BSA), and enumerated on Guava easyCyte for cellularity and enucleation rate. Remaining cells were spun down, wash once with PBS, and lysed in 20 µL high performance liquid chromatography-(HPLC) grade water. Cell debris was removed by centrifugation (10,000×g, 15 min, 4° C.). Hemolysate was stored at 70° C. until ready for globin chain analysis by reverse phase ultra performance liquid chromatography (UPLC).

Gene modification efficiency was assessed by deep DNA sequencing. The region of interest (containing the ZFN binding site within the BCL11A erythroid enhancer region) is polymerase chain reaction-(PCR) amplified and the level of modification is determined by paired end deep sequencing on an Illumina MiSeq. To generate libraries compatible with the Illumina MiSeq sequencing platform, adaptors, barcodes, and flow cell binder (short DNA sequence) were attached to the target specific amplicons using two sets of fusion primers in sequential polymerase chain reactions. The following primers are used for the MiSeq Adaptor PCR (the underlined portions are BCL11A erythroid enhancer specific sequences): PRJIYLFN f: 5' ACACGACGCTCTTC-CGATCTNNNNAGTCCTCTTCTACCCCACC (SEQ ID NO:35) and PRJIYLFN r: 5'GACGTGTGCTCTTC-CGATCTCTACTCTTAGACATAACACACC (SEQ ID NO:36). Individual single cell derived erythroid cultures were harvested, and gDNA was extracted using QuickExtract™ (Epicentre) for genotyping analysis using deep sequencing on the Illumina platform.

For globin chain analysis by reverse phase UPLC, 5 µL of hemolysate was injected onto a Waters Acquity UPLC Protein BEH C4 Column (300 A, 1.7 microm, 2.1 mm×100 mm). Elution was obtained at RT with a flow rate of 0.2 mL/min using an 18 minute linear gradient of 38% to 42.5% acetonitrile in water with trifluoroacetic acid constant at 0.1%. Elution was followed at 220 nm. Area percentage for specific globin chains, γ, β or α, representing the amount of each specific globin chains, was quantitated using Agilent OpenLAB software.

Results

For this study, 120 or 80 μg/ml SB ZFN was transfected into CD34+ cells to generate SB ZFN HSPC cells and cell samples were collected at three days post transfection and analyzed for the levels of BCL11A erythroid enhancer region disruption by deep sequencing. This revealed approximately 67% modified BCL11A alleles in the SB ZFN transfected sample for experiment 1 and 58% for experiment 2 (Table 14).

To perform such a single cell analysis, individual cells in SB ZFN HSPC from two different experiments (1 and 2), were sorted and plated in 96 well plates and underwent erythroid differentiation in vitro, and individual single cell cultures were analyzed by high throughput DNA sequencing as well as globin expression analysis by UPLC, respectively.

The MiSeq genotyping results for the single cell cultures are summarized in Table 14. For each lot of SB ZFN treated HSPC cells, between 200 300 individual single cell erythroid cultures were analyzed. Of all the clones with clear phenotypes (mixed clones excluded, 205 clones for experiment 1 and 265 clones for experiment 2), 28 or 36% are wild type clones (+/+), 14 or 11% are heterozygous clones (+/), and 58 or 52% are homozygous (/) clones, for experiment 1 and experiment 2, respectively. Of all alleles in the single cell erythroid cultures derived from SB ZFN treated cells, 65% or 58%, for experiments 1 and 2, respectively, were disrupted at the BCL11A erythroid enhancer locus. Of all the single cell erythroid cultures bearing any modified alleles, 81% (experiment 1) or 82% (experiment 2) of the modified cell clones had both BCL11A alleles disrupted.

TABLE 14

Genotyping of Single Cell Erythroid Cultures Derived from SB ZFN Transfected HSPC

| SB-ZFN-HSPC Lot | Experiment number #1 | #2 |
|---|---|---|
| Total clones examined | 205 | 265 |
| (Total alleles) | (410) | (530) |
| Wild-type Clones | 57 | 96 |
| (+/+) | (28%) | (36%) |
| Heterozygous Clones | 28 | 30 |
| (Monoallelic Modified) (+/−) | (14%) | (11%) |
| Homozygous Clones | 120 | 139 |
| (Biallellic Modified) (−/−) | (58%) | (52%) |
| Net Modified | 148 | 169 |
| (Heterozygous [+/−] + Biallelic modified [−/−]) | (72%) | (63%) |
| Fraction of Modified Cells which are Biallelic modified [−/−] | 81% | 82% |
| BCL11A erythroid enhancer modification in pool before single cell culture (% of total alleles) | 67% | 58% |
| % of Total Alleles Net BCL11A erythroid enhancer modification from single cell data (% of total alleles) | 65% | 58% |

The data show that a pool of SB ZFN HSPC bearing 58-67% targeted BCL11A erythroid enhancer modification was made up of 28-36% wild type cells, 11-14% cells bearing a monoallelic modification, and 52-58% cells bearing biallelic modification of the target locus.

Of the clones with clear genotypes, 152 and 172 clones (experiments 1 and 2, respectively) were successfully differentiated into erythroid cells in vitro, as indicated by enucleation rate measured by NucRed stain. These single cell erythroid cultures were then subjected to reverse phase UPLC analysis to measure globin chain expression level. Colonies differed in their degree of erythroid maturation; some variation in the γ/β globin ratio was expected even within colonies bearing the same BCL11A erythroid enhancer genotype. Furthermore, a fraction of the disrupted alleles of the BCL11A erythroid enhancer may retain partial or complete function, potentially as a result of retaining a GATA 1 binding site (Vierstra et al (2015) *Nat Methods.* 12(10): 927-30; Canver et al (2015) *Nature* 527(7577): 192-7).

Figure 13:
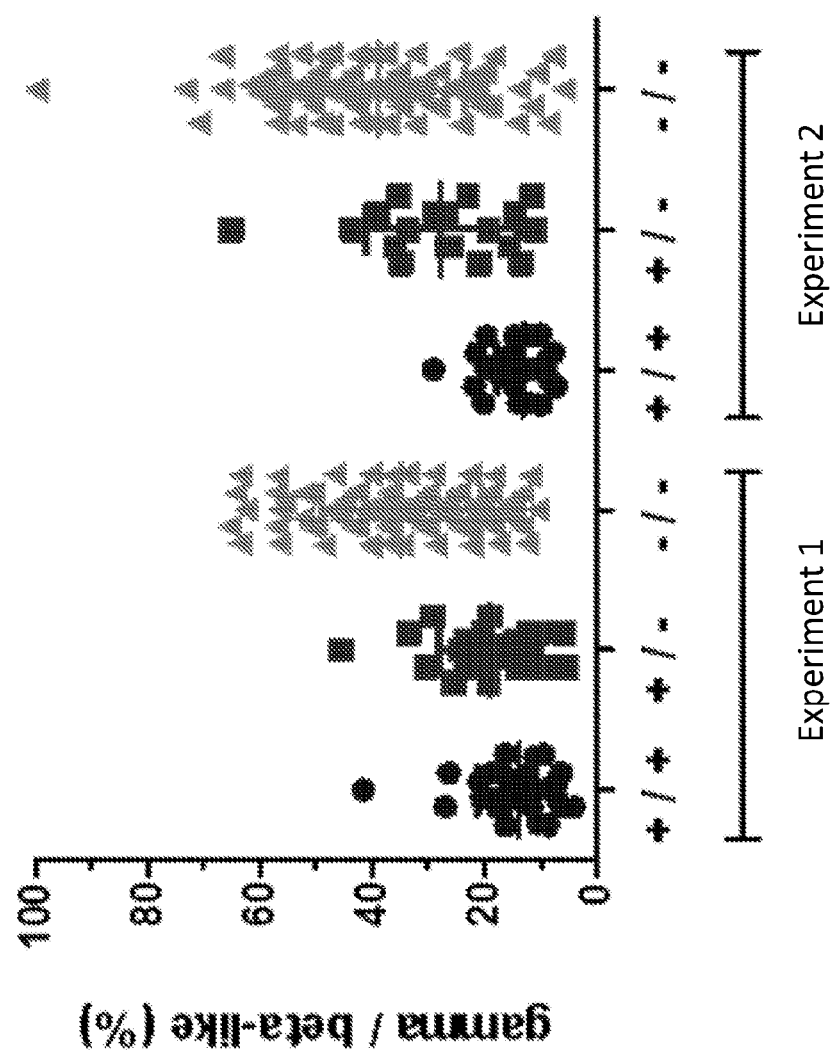
FIG. 13 shows a graph of the gamma/beta like protein ratios graphed according to the allele state in the individual colonies analyzed. The data were sorted by genotypic class ("+" for unmodified allele, "−" for edited allele; "+/+" for wild type; "+/−" for monoallelic modified; and "−/−" for biallelic modified).

As can be seen in the data (FIG. 13), the results revealed a clear correlation between the genotype of a colony for the BCL11A erythroid enhancer locus and its γ/β globin ratio. Specifically, colonies bearing a biallelic (homozygous) modification of BCL11A had a mean normalized γ/β ratio of 35% and 39% for experiments 1 and 2, respectively, colonies with a monoallelic (heterozygous) modification had a mean normalized γ/β ratio of 19% and 13% for experiments 1 and 2, respectively, and wild type colonies 14% and 13% for experiments 1 and 2, respectively. In a two tailed t test with Welch's correction, the P value of the "homozygous vs wild type" comparison are <0.0001 for both experiments 1 and 2; the P value of the "heterozygous vs homozygous" comparison are <0.0001 for experiment 1 and 0.0025 for experiment 2; and the P value of the "heterozygous vs wild type" comparison are 0.02 and 0.0002 for both experiments 1 and 2, respectively. In the graph below (FIG. 13), the γ/β and γ/α globin ratio is plotted for all the colonies assayed, sorted by the genotyping class of BCL11A erythroid enhancer alleles.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed:

1. A zinc finger protein comprising 4, 5 or 6 fingers designated F1 to F4, F1 to F5 or F1 to F6, each finger comprising a recognition helix region that recognizes a target subsite wherein the protein is selected from the group consisting of
(i) a protein comprising the recognition helix regions as follows:
F1: STGNLTN (SEQ ID NO: 7);
F2: TSGSLTR (SEQ ID NO: 5);
F3: DQSNLRA (SEQ ID NO: 2); and
F4: AQCCLFH (SEQ ID NO: 6);
(ii) a protein comprising the recognition helix regions as follows:
F1: DQSNLRA (SEQ ID NO: 2);
F2: RPYTLRL (SEQ ID NO: 3);
F3: SRGALKT (SEQ ID NO: 8);
F4: TSGSLTR (SEQ ID NO: 5);
F5: DQSNLRA (SEQ ID NO: 2); and
F6: AQCCLFH (SEQ ID NO: 6);
(iii) a protein comprising the recognition helix regions as follows:
F1: DQSNLRA (SEQ ID NO: 2);
F2: RNFSLTM (SEQ ID NO: 9);
F3: SNGNLRN (SEQ ID NO: 10) or SSYNLAN (SEQ ID NO: 11);
F4: TSGSLTR (SEQ ID NO: 5);
F5: DQSNLRA (SEQ ID NO: 2); and
F6: AQCCLFH (SEQ ID NO: 6);
(iv) a protein comprising the recognition helix regions as follows:
F1: RSDHLTQ (SEQ ID NO: 13);
F2: QSGHLAR (SEQ ID NO: 14);
F3: QKGTLGE (SEQ ID NO: 15);
F4: RHRDLSR (SEQ ID NO: 18); and
F5: RRDNLHS (SEQ ID NO: 17);
(v) a protein comprising the recognition helix regions as follows:
F1: RNDHRTT (SEQ ID NO: 19);
F2: QKAHLIR (SEQ ID NO: 20);
F3: QKGTLGE (SEQ ID NO: 15);
F4: LKRTLKR (SEQ ID NO: 25); and
F5: RRDNLHS (SEQ ID NO: 17);
(vi) a protein comprising the recognition helix regions as follows:
F1: RSDHLTQ (SEQ ID NO: 13);
F2: QRAHLTR (SEQ ID NO: 22);
F3: QKGTLGE (SEQ ID NO: 15) or QSGTRNH (SEQ ID NO:24);
F4: HRNTLVR (SEQ ID NO: 23); and
F5: RRDNLHS (SEQ ID NO: 17);
(vii) a protein comprising the recognition helix regions as follows:
F1: RSDHLTQ (SEQ ID NO: 13);
F2: QKAHLIR (SEQ ID NO: 20);
F3: QKGTLGE (SEQ ID NO: 15) or QSGTRNH (SEQ ID NO: 24);
F4: RGRDLSR (SEQ ID NO: 21); and
F5: RRDNLHS (SEQ ID NO: 17); and
(viii) a protein comprising the recognition helix regions as follows:
F1: RSDHLTQ (SEQ ID NO: 13);
F2: QSGHLAR (SEQ ID NO: 14);
F3: QSGTRNH (SEQ ID NO: 24);
F4: QSSDLSR (SEQ ID NO: 16); and
F5: RRDNLHS (SEQ ID NO: 17).

2. A fusion protein comprising the zinc finger protein of claim 1 and a functional domain.

3. The fusion protein of claim 2, wherein the functional domain is a transcriptional activation domain, a transcriptional repression domain, or a cleavage domain.

4. A polynucleotide encoding the zinc finger protein of claim 1.

5. An isolated cell comprising the fusion protein of claim 2, wherein the fusion protein is expressed in the cell.

6. The isolated cell of claim 5, wherein the cell is a hematopoietic stem cell or an erythroid precursor cell.

7. The isolated cell of claim 6, wherein the cell is a human cell.

8. The isolated cell of claim 6, wherein the genome of the cell is modified by the fusion protein.

9. The isolated cell of claim 8, wherein the genomic modification is selected from the group consisting of insertions, deletions and combinations thereof.

10. The isolated cell of claim 8, wherein the genomic modification is within the +58 region of the BCL11A enhancer sequence.

11. An isolated, genetically modified progeny cell or cell line produced from the cell of claim 10.

12. An isolated, genetically modified partially or fully differentiated cell descended from the progeny cell or cell line of claim 11.

13. The isolated cell of claim 10, wherein the functional domain is a cleavage domain and further wherein the cell exhibits increased expression of gamma and/or beta globin as compared to a cell without the genomic modification.

14. A pharmaceutical composition comprising the cell of claim 5.

15. A method of modifying the endogenous BCL11a enhancer sequence within intron 2 of the BCL11a gene in a cell, the method comprising administering to the cell a polynucleotide encoding the fusion protein of claim 3, wherein the functional domain is a cleavage domain such that the endogenous BCL11a enhancer sequence is modified.

16. The method of claim 15, further comprising introducing an exogenous sequence into the cell such that the exogenous sequence is inserted into the endogenous BCL11a enhancer sequence.

17. The method of claim 15, wherein the modification comprises a deletion.

18. A method of increasing globin production in a subject, the method comprising administering the cell of claim 13 to the subject.

19. The method of claim 18, wherein the subject is a human and the cell is a human cell.

20. The method of claim 19, wherein the cell is administered to the bone marrow of the subject and wherein the cell engrafts, differentiates and matures in the subject.

21. The method of claim 18, wherein the subject has a hemoglobinopathy.

22. The method of claim 21, wherein the hemoglobinopathy is a beta-thalassemia or sickle cell disease.

23. A method of producing a genetically modified cell comprising a genomic modification within the endogenous BCL11a enhancer sequence within intron 2 of the BCL11a gene, the method comprising the steps of:
   a) contacting the cell with a polynucleotide encoding the fusion protein of claim 2, wherein the functional domain is a cleavage domain; and
   b) subjecting the cell to conditions conducive for expressing the fusion protein, wherein the expressed fusion protein modifies the endogenous BCL11A enhancer sequence to produce the genetically modified cell.

24. The method of claim 23, further comprising stimulating the cell with at least one cytokine.

25. A kit comprising the polynucleotide of claim 4.

* * * * *